United States Patent [19]

Zomaya et al.

[11] 4,427,689
[45] Jan. 24, 1984

[54] CLAVULANIC ACID 9-DEOXY-9-THIA DERIVATIVES THEIR PREPARATION AND USE

[75] Inventors: Iskander I. Zomaya, Worcester Park; John S. Davies, Reigate, both of England

[73] Assignee: Beecham Group Limited, England

[21] Appl. No.: 71,731

[22] Filed: Aug. 31, 1979

[30] Foreign Application Priority Data

Sep. 5, 1978 [GB] United Kingdom ............... 35642/78

[51] Int. Cl.³ .................. C07D 498/04; A61K 31/42; A61K 31/545; A61K 31/43
[52] U.S. Cl. ................................. 424/272; 260/245.3; 424/248.55; 424/248.52; 424/271; 542/413; 542/427
[58] Field of Search ...................... 260/245.3; 542/427, 542/413; 424/272

[56] References Cited

FOREIGN PATENT DOCUMENTS 2708330 9/1977 United Kingdom .

Primary Examiner—Mark L. Berch
Attorney, Agent, or Firm—Jacobs & Jacobs

[57] ABSTRACT

The compounds of the formula (I):

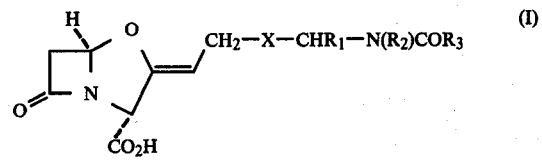

and salts and esters thereof wherein $R_1$ is a hydrogen atom or a lower alkyl, aryl or aralkyl group, $R_2$ and $R_3$ are independently hydrogen, aryl, aralkyl, lower alkyl or substituted lower alkyl, or $R_3$ is joined to $R_1$ to form a 5- or 6- membered ring and X is S, SO or $SO_2$; have been found to be β-lactamase inhibitors and antibacterial agents. Their preparation and use is described.

89 Claims, No Drawings

CLAVULANIC ACID 9-DEOXY-9-THIA DERIVATIVES THEIR PREPARATION AND USE

The present invention relates to new derivatives of clavulanic acid, to pharmaceutical compositions containing them and to a process for their preparation.

In Belgian Pat. No. 850779, it was disclosed that thioethers of clavulanic acid could be prepared by the reaction of an ester of clavulanic acid with a thiol or other thioetherifying agent. The later published French Pat. No. 2342292 also related to thioethers of clavulanic acid. It has now been found that certain novel thiol derivatives can be prepared that offer a useful range of β-lactamase inhibitory properties and so serve to enhance the spectrum of penicillins and cephalosporins. In addition these compounds have antibacterial properties.

The present invention provides the compounds of the formula (I):

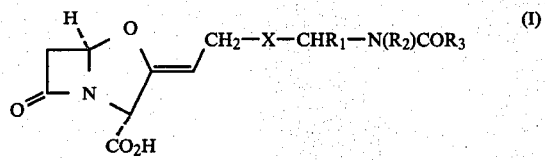

and salts and esters thereof wherein $R_1$ is a hydrogen atom or a lower alkyl, aryl or aralkyl group, $R_2$ and $R_3$ are independently hydrogen, aryl, aralkyl, lower alkyl or substituted lower alkyl, or $R_3$ is joined to $R_1$ to form a 4-, 5- or 6-membered ring or is joined to $R_2$ to form a 5- or 6-membered ring and X is S, SO or $SO_2$.

When used herein the term "lower" means that the group contains not more than 6 carbon atoms and more suitably not more than 4 carbon atoms.

When used herein the term "aryl" means a phenyl, thienyl or furyl group or a phenyl group substituted by a fluorine or chlorine atom or a lower alkyl or lower alkoxy group.

When used herein the term "aralkyl" means a lower alkyl group substituted by an aryl group.

When used herein the term "substituted alkyl" means a lower alkyl group substituted by a lower alkoxy group, an aryloxy group, a carboxylic acid group or a salt or lower alkyl or aralkyl ester of said carboxylic acid group or by an amino group or an aryl group.

When used herein the term "aryloxyalkyl" means a lower alkyl group substituted by an O-aryl group.

Suitably the compound of this invention is of the formula (II):

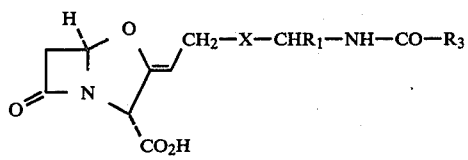

or a salt thereof wherein $R_1$ is a hydrogen atom and $R_3$ is a hydrogen atom or an aryl, aralkyl, lower alkyl or substituted lower alkyl group or $R_1$ and $R_3$ are joined so that the $CHR_1NH.CO.R_3$ moiety forms a group of the sub-formula (a):

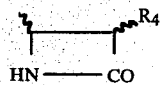

wherein $R_4$ is a hydrogen atom or a $NH.CO.R_5$ group wherein $R_5$ is a lower alkyl, lower alkoxy lower alkyl, aryl, aralkyl, aryloxyalkyl, lower alkoxy or aryloxy group and X is S, SO or $SO_2$.

One suitable sub-group of compounds of the formula (II) are those of the formula (III):

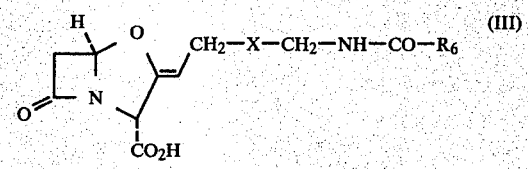

and salts and esters thereof wherein $R_6$ is a hydrogen atom or an aryl, aralkyl, lower alkyl or substituted lower alkyl group and X is S, SO or $SO_2$.

Suitably $R_6$ is a hydrogen atom; an alkyl group of up to 4 carbon atoms; an alkyl group of up to 4 carbon atoms substituted by an alkoxy group of up to 4 carbon atoms; a phenyl group; a phenyl group substituted by a fluorine or chlorine atom or a methyl or methoxyl group; a benzyl group; or a benzyl group substituted by a fluorine or chlorine atom or a methyl or methoxyl group.

Favoured values for $R_6$ include the methyl group, the ethyl group and the phenyl group.

A further suitable sub-group of compounds of the formula (II) are those of the formula (IV)

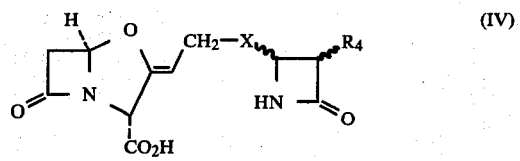

and salts and esters thereof wherein $R_4$ is as defined in relation to sub-formula (a) and X is S, SO or $SO_2$.

Suitably $R_4$ is a hydrogen atom.

Suitably $R_4$ is a $NH.CO.R_7$ group where $R_7$ is an alkyl group of up to 4 carbon atoms; an alkyl group of up to 4 carbon atoms substituted by an alkoxy group of up to 4 carbon atoms; an aryl group; an aralkyl group; or an aryloxyalkyl group. Similarly $R_7$ may be an alkoxy group of up to 4 carbon atoms or an aryloxy group.

Favoured values for $R_7$ include the methyl, ethyl, phenyl, benzyl, phenoxymethyl, p-methoxyphenyl, p-methoxyphenoxymethyl, ethoxyethyl and like groups.

A further suitable sub-group of compounds of the formula (I) is that of the formula (V):

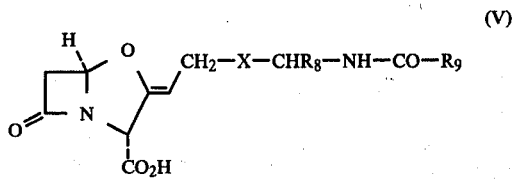

and salts and esters thereof wherein $R_8$ is a lower alkyl, aryl or aralkyl group, $R_9$ is a hydrogen atom or an aryl, aralkyl, lower alkyl or substituted lower alkyl group and X is S, SO or SO$_2$.

Suitable values for R$_8$ include methyl, ethyl, n-propyl, n-butyl and phenyl. A favoured value for R$_8$ is the methyl group.

Suitably R$_9$ is a hydrogen atom; an alkyl group of up to 4 carbon atoms; an alkyl group of up to 4 carbon atoms substituted by an alkoxy group of up to 4 carbon atoms; a phenyl group; a phenyl group substituted by a fluorine or chlorine atom or a methyl or methoxyl group; a benzyl group; or a benzyl group substituted by a fluorine or chlorine atom or a methyl or methoxyl group.

Favoured values for R$_9$ include the methyl group, the ethyl group and the phenyl group.

Another suitable sub-group of compounds of the formula (I) is that of the formula (VI):

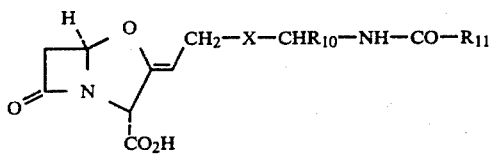

and salts and esters thereof wherein R$_{10}$ is a hydrogen atom or a lower alkyl group and R$_{11}$ is a lower alkyl group substituted by an amino group and optionally by an aryl group or R$_{10}$ and R$_{11}$ are joined so that the CHR$_{10}$—NH—CO—R$_{11}$ moiety forms a group of the sub-formula (b):

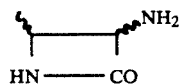

and X is S, SO or SO$_2$.

Suitably R$_{10}$ is a hydrogen atom. Suitably R$_{10}$ is a methyl, ethyl, n-propyl or n-butyl group of which methyl and ethyl are preferred.

One suitable sub-group of compounds of the formula (VI) is that of the formula (VII):

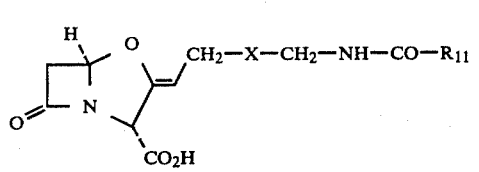

and salts and esters thereof wherein R$_{11}$ is an alkyl group of up to 4 carbon atoms substituted by an amino group or R$_{11}$ is an alkyl group of up to 4 carbon atoms substituted by an amino group and by an aryl group and X is S, SO or SO$_2$.

Favoured values for R$_{11}$ include those groups wherein the amino substituent is on the α-carbon atom, for example the aminomethyl, α-aminoethyl, α-aminobenzyl and like groups.

A further suitable sub-group of compounds of the formula (VI) are the compound of the formula (VIII):

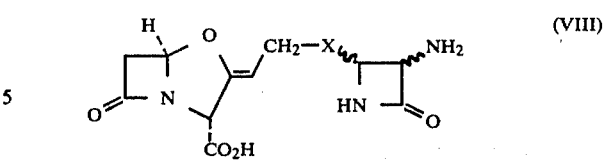

and salts and esters thereof wherein X is S, SO or SO$_2$. The compound of the formula (VIII) may have the cis- or trans-stereochemistry about the monocyclic β-lactam or may be in the form of mixtures of such compounds.

Another suitable sub-group of compounds of the formula (I) are those of the formula (IX):

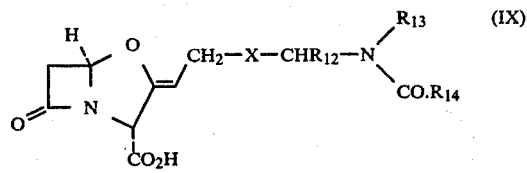

and salts and esters thereof wherein R$_{12}$ is a hydrogen atom or a lower alkyl, aryl or aralkyl group, R$_{13}$ is an aryl, aralkyl, lower alkyl or substituted lower alkyl group and R$_{14}$ is a lower alkyl group or is joined to R$_{12}$ to form a 4-, 5- or 6-membered ring or is joined to R$_{13}$ to form a 5- or 6-membered ring and X is S, SO or SO$_2$.

Suitable acyclic values for R$_{12}$ include the hydrogen atom and the methyl, ethyl, n-propyl, n-butyl and phenyl groups. The hydrogen atom is a particularly suitable acyclic value for R$_{12}$, as is the methyl group.

Suitable acyclic values for R$_{13}$ include an alkyl group of up to 4 carbon atoms; an alkyl group of up to 4 carbon atoms substituted by an alkoxy group of up to 4 carbon atoms; a phenyl group; a phenyl group substituted by a fluorine or chlorine atom or a methyl or methoxyl group; a benzyl group; or a benzyl group substituted by a fluorine or chlorine atom or a methyl or methoxyl group.

Favoured acyclic values for R$_{13}$ include the methyl group, the ethyl group and the phenyl group and the optionally salted or esterified carboxymethyl group.

Suitable values for —CHR$_{12}$—N(R$_{13}$)COR$_{14}$ when R$_{12}$ and R$_{14}$ are linked include those of the sub-formula (c):

wherein n is 1, 2 or 3 and R$_{13}$ is an acylic moiety as defined in relation to formula (VII).

Suitable values for —CHR$_{12}$—N—(R$_{13}$)COR$_{14}$ when R$_{13}$ and R$_{14}$ are linked include those of the sub-formula (d):

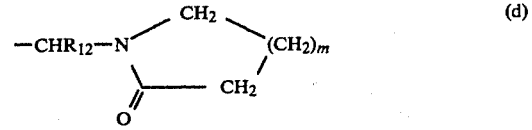

wherein m is 1 or 2 and R$_{12}$ is an acylic moiety as defined in relation to formula (IX).

Favourably in relation to sub-formula (c) n is 1 and $R_{13}$ is an optionally salted or esterified carboxymethyl group.

Favourably in relation to sub-formula (d) $R_{12}$ is a hydrogen atom.

A preferred aspect of this invention is provided by the compound of the formula (X):

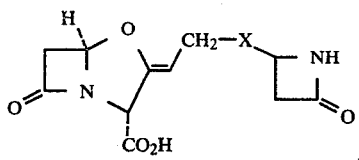 (X)

and salts and esters thereof wherein X is S, SO or $SO_2$.

Pharmaceutically acceptable salts of the compounds of the formula (X) are particularly preferred aspect of this invention.

Further favoured aspects of this invention are provided by the compounds of the formulae (XI)–(XIV):

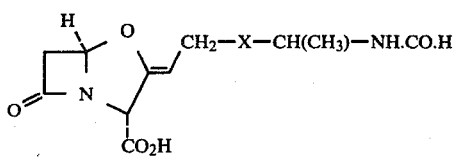 (XIa)

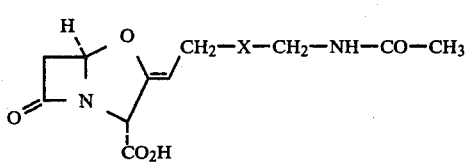 (XIb)

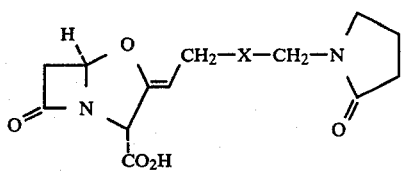 (XII)

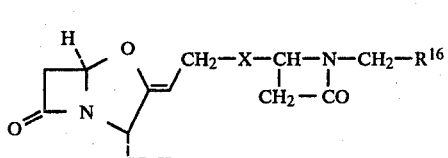 (XIII)

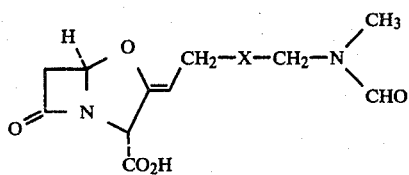 (XIV)

and salts and esters thereof wherein $R^{16}$ is H or $CO_2H$ and X is S, SO or $SO_2$.

The compounds of the formula (I) are aptly presented as the free acid per se or as a salt thereof and are more aptly in the form of a pharmaceutically acceptable salt.

Suitably the compounds of the formula (I) are presented as the free acid but more favourably the compounds of the formula (I) are in the form of a salt. Apt salts include alkali or alkaline earth metal salts such as the lithium, sodium, potassium, calcium or magnesium salts. Other apt salts include the amonium salt and salts of amines such as lower alkylamine salts such as methylamine, ethylamine, dimethylamine or the like salts or salts of cyclic bases such as pyrrolidine or quaternary amonium salts such as the tetramethyl ammonium salt. Particularly suitable salts include the lithium (for use as an intermediate), sodium, potassium, calcium and magnesium salts. A preferred salt is the sodium salt. Another preferred salt is the potassium salt. A further preferred salt is the lithium salt. An additional preferred salt is the magnesium salt. An alternative preferred salt is the t-butylamine [$(CH_3)_3CHN_2$] salt.

The preceding salts are also favoured in relation to the compounds of the formulae (II), (III) and (VII)–(XII). An exception to the preceding rule occurs when the compound of the formula (I) contains an amino group. In this circumstance the compound of the formula (I) is most suitably zwitterionic.

Since the salts of the compounds of this invention are primarily for pharmaceutical use, the reader will appreciate that pharmaceutically acceptable salts are particularly preferred.

Suitable esters of the compounds of the formulae (I)–(XII) include those of the sub-formulae (e) and (f):

 (e)

 (f)

wherein $A^1$ is an alkyl group of 1–6 carbon atoms optionally substituted by an alkoxyl or acyloxy group of 1–7 carbon atoms; $A^2$ is an alkenyl group of up to 5 carbon atoms or is a phenyl group optionally substituted by a fluorine, chlorine, bromine, nitro or alkyl or alkoxyl of up to 4 carbon atoms; and $A^3$ is a hydrogen atom, an alkyl group of up to 4 carbon atoms or a phenyl group optionally substituted by a fluorine, chlorine, bromine, nitro or alkyl or alkoxyl of up to 4 carbon atoms.

When used herein "acyloxy" has its usual meaning of unsubstituted carboxylic acyl.

Certain favoured groups $A^1$ include the methyl, ethyl, methoxymethyl, acetoxymethyl, acetoxyethyl, phthalidyl, ethoxycarbonyloxymethyl, α-ethoxycarbonyloxyethyl, pivaloyloxymethyl and the like groups.

Certain favoured groups $A^2$ include the phenyl, methoxyphenyl and nitrophenyl groups. A particularly favoured moiety $A^3$ is the hydrogen atom.

The salts of the compounds of the formulae (I)–(XIV) are envisaged primarily as pharmaceutical agents although they may also be employed as intermediates, for example in preparing other salts or in the preparation of the parent acid or in the preparation of esters. The compounds of the formulae (I)–(XIV) are envisaged primarily as intermediates in the preparation of the non-toxic salts but may also be employed as pharmaceutical agents.

The compounds of the invention in which the side chain carbon atom between the oxygen and nitrogen atoms is substituted by other than hydrogen may be in the R- or S-forms although for convenience of preparation the R,S-mixture is advantageous.

In any of the compounds of formulae (I) to (XIV) X is aptly S.

In any of the compounds of the formulae (I) to (XIV) X is aptly SO.

In any of the compounds of the formulae (I) to (XIV) X is aptly SO₂. Such compounds are advantageous since they are less oderiferous than those wherein X is S or even SO. Additionally these compounds are more stable and easier to handle than those of lower oxidation level.

The present invention also provides a pharmaceutical composition which comprises a compound of this invention and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics such as β-lactam containing antibiotics. Such compositions may be formulated in known manner, for example by mixing. Favourably such formulations are manufactured in a dry environment and are formulated from dry ingredients.

Injectable or infusable compositions of salts of a compound of the formula (I) are particularly suitable as high blood level of a compound of the formula (I) can occur after administration by injection or infusion. Thus, one preferred composition aspect of this invention comprises an injectable salt of a compound of the formula (I) in sterile form, for example the sterile sodium or potassium salt.

Most suitably the composition is in unit dosage form. Unit dose compositions comprising a compound of the formula (I) or a salt or ester thereof adapted for oral administration form a further preferred composition aspect of this invention.

Compositions of this invention preferably comprise a non-toxic salt of a compound of the invention, for example a sodium or potassium salt or a salt with a non-toxic amine. A preferred salt for this use is the sodium salt. Another preferred salt for this use is the potassium salt.

The compound of the formula (I) or its salt or ester may be present in the composition as sole therapeutic agent or it may be present together with other therapeutic agents such as a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriaxine, pirbenicillin, α-sulphonyloxybenzylpenicillin, cephaloridine, cephalothin, cefazolin, cephalexin, cephacetrile, cephamandole nafate, cephapirin, cephradine, 4-hdroxycephalexin, cefaparole, cephaloglycine, and other well known penicillins and cephalosporins or pro-drugs therefor such as hetacillin metampicillin, 4-acetoxyampicillin, the acetoxymethyl, αethoxycarbonyloxyethyl, pivaloyloxymethyl or phthalidyl esters of ampicillin or amoxycillin or the phenyl, tolyl or indanyl esters of carbenicillin or ticarcillin or the like. Such compounds are frequently used in the form of a hydrate and/or salt such as a sodium or potassium salt of a carboxyl group, or hydrochloride of amine functions and the like. Mezlocillin and azolcillin and their salts are also apt.

Naturally if the penicillin or cephalosporin present in the composition is not suitable for oral administration then the composition will be adapted for parenteral administration.

When present together with a cephalosporin or penicillin, the ratio of a compound of the formula (I) or its salt or ester present to the other antibacterial agent may vary over a wide range of ratios, for example 3:1 to 1:10 and advantageously may be from 1:1 to 1:8, for example, 1:2, 1:3, 1:4, 1:5 or 1:6.

The total quantity of compound of the formula (I) in any unit dosage form will normally be between 25 and 1000 mg and will usually be between 50 and 500 mg for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day of treatment but more usually between 100 and 750 mg of the compounds of the invention will be administered per day, for example as 1-6 doses, more usually 2-4 doses, for example as 3 doses.

The penicillin or cephalosporin in synergistic compositions of this invention will normally be present at approximately the amount at which it is conventionally used.

Particularly favoured compositions of this invention will contain from 150–1000 mg of amoxycillin, ampicillin or a pro-drug therefor and from 25–500 mg of a compound of the formulae (I)–(XIV) or a salt or ester thereof and more suitably from 200–750 mg of amoxycillin or a salt thereof and from 50–250 mg of a salt of a compound of the formulae (I)–(XIV).

Most suitably a pharmaceutically acceptable salt of the compound of the formula (X) is used.

Most suitably this form of the composition will comprise ampicillin or its salt or amoxycillin or its salt. The ampicillin is suitably present as ampicillin anhydrate, ampicillin trihydrate or sodium ampicillin. The amoxycillin is suitably present as amoxycillin trihydrate or sodium amoxycillin. The orally administrable compositions will normally comprise the zwitterion and the injectable composition will normally comprise the sodium salt. Amoxycillin Trihydrate and sodium amoxycillin are particularly preferred.

Other particularly favoured compositions of this invention will contain from 150–1000 mg of carbenicillin, ticarcillin or a pro-drug therefor and from 25–500 mg of a compound of the formulae (I)–(XIV) or a salt or ester thereof and more suitably from 200–750 mg of ticarcillin and from 50–250 mg of a salt of a compound of the formulae (I)–(XIV).

Naturally the salts will be pharmaceutically acceptable.

Particularly suitable salts of carbenicillin and ticarcillin are their dis-sodium salts. Suitable pro-drugs include salts, usually the sodium salt, of the α-phenyl and α-indanyl esters. Compositions containing the di-salts of the penicillins will be adapted for injectable administration and the penicillin esters will be used for oral administration.

Other particularly favoured compositions of this contain cefazolin or more suitably a pharmaceutically acceptable salt such as its sodium salt. These compositions will be adapted for administration by injection.

The weights of the antibiotics in such compositions are expressed on the basis of antibiotic per se theoretically available from the composition.

The compositions of this invention may be used to treat infections caused by strains of Gram-positive and Gram-negative bacteria such as *Staphylococcus aureus, Escherichia coli, Klebsiella aerogenes, Haemophilus influenzae, Neisseria gonorrhoeae, Proteus mirabilis, Proteus vulgaris, Pseudomonas aeruginosa, Bacteroides fragilis* and the like including many β-lactamase producing strains, for example also of *Brannamella catarrhalis.*

The compositions of this invention may be administered so that the therapeutic effect is achieved without any clear signs of acute toxicity being seen.

The compositions of this invention may benefit from formulation under dry conditions.

The present invention provides a process for the preparation of compounds of the formula (I) or a salt or ester thereof, which comprises the reaction of an ester of 9-mercaptodeoxyclavulanic acid with a compound of the formula (XV):

$$Y-CHR_1-NR_2-CO-R_3 \quad (XV)$$

wherein $R_1$, $R_2$ and $R_3$ are as defined in relation to formula (I) and Y is a displaceable group; and thereafter, if desired, converting the thus produced ester into the free acid or a salt thereof, and/or, if desired, converting the compound wherein X is S into a compound wherein X is SO or $SO_2$.

Suitable moieties Y include conventional displaceable groups such as carboxylate esters such as $O.CO.R^{15}$ or $O.CO.OR^{15}$ where $R^{15}$ is an inert organic group such as a lower alkyl group (such as a methyl, ethyl, propyl or butyl group), a phenyl, benzyl, methoxyphenyl, methylphenyl, halophenyl, nitrophenyl or like group; or a $O.CO.H$ group; or other moiety displaceable by a nucleophile such as a halogen atom, for example chlorine or bromine atom; or a hydroxyl group.

Generally the process of this invention will take place in the presence of a catalyst such as zinc diacetate or its chemical equivalent when Y is a carboxylate ester or in the presence of a non-nucleophilic base and/or silver oxide and/or a soluble silver salt when Y is a halogen atom or in the presence of a Lewis acid such as borontrifluoride (for example as the etherate) or dehydrating agent such as p-toluene sulphonic acid when Y is a hydroxyl group.

Naturally any amino group optionally present in the compound of formula (XV) will be protected during the thioetherification and the protecting group removed thereafter.

The thioetherification may be carried out at a non-extreme depressed, ambient or elevated temperature such as −10° to 120° C.; for example the temperature of the reaction may be slightly or moderately elevated (for example 30° to 100° C.) when employing zinc acetate as a catalyst or depressed (for example 0° to 15° C.) when $BF_3$ is used as a catalyst.

The thioetherification reaction is generally carried out in an inert non-hydroxylic medium such as a hydrocarbon, halohydrocarbon or ester solvent, for example benzene, toluene, methylene chloride, ethyl acetate, chloroform, or mixtures thereof.

The present invention also provides a process for the preparation of a compound of the formula (I) or a salt or ester thereof which comprises the reaction of an ester of a compound of the formula (XVI):

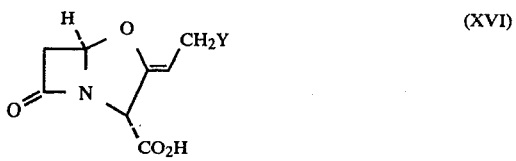

wherein Y is a displaceable group with a thiol of the formula (XVII):

$$HS-CHR_1-NR_2-CO-R_3 \quad (XVII)$$

or a salt thereof wherein $R_1$, $R_2$ and $R_3$ are as defined in relation to formula (I) and Y is as defined in relation to formula (XV); and thereafter if desired, converting the thus produced ester into the free acid or a salt thereof; and/or if desired, converting the compound wherein X is S into a compound wherein X is SO or $SO_2$.

This process of the reaction may be performed in non-hydroxylic solvent such as dimethylformamide or the like at a non-extreme temperature such as 0° to 30° C. and conveniently at ambient temperature.

It is frequently convenient that if the compound of the formula (XVII) per se is used then an acid acceptor is also present, for example a tertiary amine such as triethylamine.

Naturally any amino group optionally present in the compound of the formula (XVII) will be protected during the thioetherification reaction and the protecting group removed thereafter.

After the reaction is complete, the desired ester can be obtained by evaporation of the solvent and purification of the product chromatographically for example by gradient elution using solvent mixtures such as ethyl acetate/cyclohexane or ethyl acetate/petroleum ether (60°–80°) using silica gel or the like as stationary phase.

In a further aspect the present invention also provides a process for the preparation of compound of the formula (I) or a salt thereof which comprises the de-esterification of an ester of the compound of the formula (I) optionally in the presence of a base.

Such de-esterification may involve hydrolysis or hydrogenolysis. Thus for example an ester such as a methyl, ethyl, methoxymethyl, ethoxymethyl, acetoxymethyl or like ester may be subjected to mild base hydrolysis to yield a salt of a compound the formula (I). Suitably these esters may be hydrolysed by maintaining the pH of the medium at 7.5 to 9 until the hydrolysis is effected. Most suitably a readily hydrolysable ester such as the methoxymethyl ester is employed in this process. The pH may be maintained in the desired range in a pH-stat by the addition of a solution or suspension of a base such as LiOH, NaOH, KOH, $Ca(OH)_2$, $Mg(OH)_2$, $NaHCO_3$, $Na_2CO_3$, $MgCO_3$ or the like at a rate that prevents the accumulation of excess base which would cause the pH to increase unacceptably.

Suitable methods of hydrogenolysis of esters of the compounds of formula (I) include hydrogenation in the presence of a transition metal catalyst. Suitable hydrogenolysable esters of the compound of the formula (I) include those where the ester moiety is of the sub-formula $CO_2CHA^2A^3$ as hereinbefore defined and of these the benzyl and p-methoxybenzyl esters are particularly suitable. The p-nitrobenzyl ester is a preferred ester.

The pressure of hydrogen used in the reaction may be low, medium or high but in general an approximately atmospheric or slightly superatmospheric pressure of hydrogen is preferred. The transition metal catalyst employed is preferably palladium, for example palladium on charcoal, palladium or barium sulphate, palladium on calcium carbonate or the like. The hydrogenation may be effected in any convenient solvent in which the ester is soluble such as tetrahydrofuran, ethyl acetate, ethanol, aqueous ethanol or the like. If this hydrogenation is carried out in the presence of a base then a salt of the compounds of formula (I) is produced. Suitable bases for inclusion include $NaHCO_3$, $Na_2CO_3$, $K_2CO_3$, $CaCO_3$, $MgCO_3$, $LiHCO_3$, $N(C_2H_5)_3.HO_2C.CH_3$ and the like. If no base is present then hydrogenation leads to the preparation of an acid of formula (I) which may then be neutralised if desired to yield a salt. Suitable bases for such neutralisation include LiOH, $NaHCO_3$, KOH, $Ca(OH)_2$, $Ba(OH)_2$, $Mg(OH)_2$, $NH_4OH$, $N(C_2H_5)_3$, $N(C_2H_5)_3.HO_2CCH_3$, Na ethylhexanoate, K ethylhexanoate and the like e.g. MgO and $NH_2C(CH_3)_3$.

The lithium salts of the compounds of formula (I) tend to be more easily prepared in pure crystalline form than other salts of the compounds of formula (I). It is therefore often convenient to first form the lithium salt and then convert this into a further salt by ion-exchange, for example by passing a solution of the lithium salt through a bed of a cation exchange resin in sodium, potassium, calcium, ammonium or like form. Suitable cation exchange resins include Amberlite IR 120 and equivalent resins. Another salt suitable for use as an intermediate in this way is the t-butylamine salt.

The zwitterions of the formulae (VI) to (VIII) are normally formed by a simultaneous de-esterification and de-protection reaction. A de-esterification/de-protection reaction convenient for laboratory use comprises the catalytic hydrogenation of a compound containing benzyloxycarbonylamino group and a benzyl ester. This reaction preferably uses a palladium catalyst such as palladium on charcoal and may employ a low, ambient or high pressure of hydrogen. The hydrogenation is generally carried out in an organic solvent at a non-extreme temperature, for example in aqueous tetrahydrofuran at ambient temperature.

Other amine protecting groups which may be employed include the azido group, the protonated amino group, enamine protected forms and the like. These may also be removed by mild processes such as reduction of an azide, hydrolysis of an enamine (such as that derived from a β-ketoacid ester such as ethylacetoacetate) or the like method.

Crystalline salts of the compounds of the formula (I) may be solvated, for example hydrated.

The salts (for example the sodium salt) of the compounds of formula (I) may be converted into the corresponding esters in conventional manner, for example by reaction with a reactive halide in solution in dimethylformamide or like solvent. Esters may similarly be prepared by the reaction in an inert solvent of a compound of formula (I) with a diazocompound or with an alcohol in the presence of a condensation promoting agent such as dicyclohexylcarbodiimide. Other reagents for use in this manner include triethyloxonium tetrafluoroborate or the like. Suitable reactive halides for use in the above process include phthalidyl bromide, pivaloyloxymethyl bromide, benzyl bromide, methyl iodide and the like.

Amino functions will normally be protected during the reaction.

A favoured process of this invention comprises the reaction of an ester of 9-mercaptodeoxyclavulanic acid with a compound of the formula (XVIII):

wherein $R_4$ is as defined in relation to formula (I) and $Y^1$ is a group of the formula $O.CO.R^{15}$ wherein $R^{15}$ is as defined in relation to formula (XV); and thereafter if desired converting the initially produced ester of the compound of the formula (IV) to the acid of the formula (IV) or its salt.

Most suitably in this process $R^{15}$ is a lower alkyl, aryl or aralkyl group.

Preferably in this process $Y^1$ is an acetoxy group.

Preferably in this process $R_4$ is hydrogen.

This process may be brought about using the general reaction conditions hereinbefore described.

The present invention also provides a process for the preparation of a compound of the formula (I) or a salt or ester thereof wherein X is SO or $SO_2$ which process which comprises oxidizing the corresponding compound wherein X is S.

Apt methods of oxidation include oxidation by an organic per-acid such as m-chloroperbenzoic acid or the like. This reagent may be employed as described in Belgian Pat. No. 850779.

The following Examples illustrate the invention. In the Examples PNB means p-nitrobenzyl.

EXAMPLE 1 p-Nitrobenzyl 9-deoxy-9-thio(azetidin-2'-on-4'-yl)clavulanate

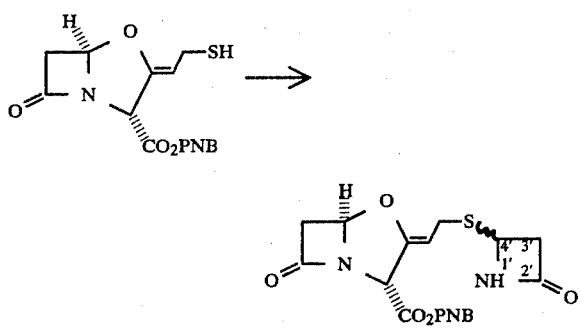

4-Nitrobenzyl (3R, 5R, Z)-2-(2-mercaptoethylidene)-clavam-3-carboxylate (55 mg; 0.156 m.mole), (±)4-acetoxyazetidinone (20 mg) and zinc acetate dihydrate (catalytic amount) were heated under reflux in benzene (8 ml) for 3 hr. (azetropically removing water). The solution was filtered and the filtrate evaporated. The residue was fractionated on silica-gel with ethyl acetate-petrol (2:3) as eluant to give the title compound (51 mg; 79%), an oil comprising a mixture of two diastereoisomers, $\nu_{max}$ ($CHCl_3$) 1810, 1770 and 1530 $cm^{-1}$; n.m.r ($CDCl_3$), δ 2.7–3.7 (6H, m, 6—$CH_2$, 9—$CH_2$, 3'—$CH_2$), 4.55–4.89 (2H, m, 8—$CH$ and 4'—$CH$), 5.12 (1H, s, 3—$CH$), 5.28 (2H, s, —$CO_2CH_2$), 5.69 (1H, m, 5—$CH$), 6.46 (1H, m, $NH$), 7.5 and 8.21 (4H, 2d, Ar—$H$).

$[\alpha]_D^{20}$ —7.7° (C. 0.43; $CHCl_3$)

EXAMPLE 2

Sodium 9-deoxy-9-thio-(azetidin-2'-on-4'-yl) clavulanate

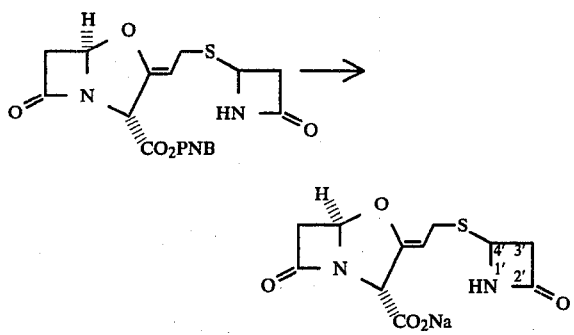

p-Nitrobenzyl 9-deoxy-9-thio-(azetidin-2'-on-4'-yl) clavulanate (43 mg; 0.103 m.mole) in tetrahydrofuran (3 ml) was added to a prehydrogenated suspension of 10% Pd/C (50 mg) in tetrahydrofuran (5 ml) and the mixture hydrogenated at 1 atmosphere for 2 hr. After filtration through celite, a solution of sodium bicarbonate (8.6 mg) in water (1 ml) was added together with more water (2 ml). The aqueous solution was washed twice with ether (5 ml) and freeze-dried to give sodium 9-deoxy-9-thio-(azetidin-2'-on-4'-yl) clavulanate as a solid (25 mg; 81%); $v_{max}$ KBr 1780, 1740 and 1610 cm$^{-1}$; δ (D$_2$O); (CH$_3$CN internal standard at 2.00 ppm) 2.7–3.8 (6H, m, 6—CH$_2$, 3'—CH$_2$, 9—CH$_2$), 4.25–5.1 (3H, m, 3—CH, 8—CH, 4'—CH), 5.7 (1H d, 5—CH).

EXAMPLE 3 p-Nitrobenzyl 9-deoxy-9-thio[3'(R)phenoxyacetamido-2-oxoazetidin-4(R)-yl] calvulanate

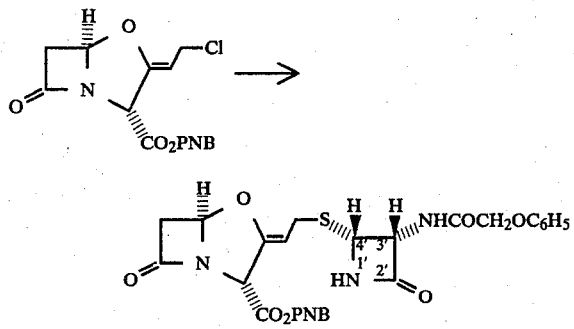

A solution of 9-chlorodeoxyclavulanate (0.352; 1 m.mole) and 4-mercapto-3-phenoxyacetamidoazetidin-2-one (0.277 g; 1.1 m.mole) in dry dimethylformamide (5 ml) was treated with triethylamine (0.14 ml) and the solution stirred at ambient temperature for 30 min. The solution was diluted with diethylether (50 ml) and the organic layer washed successively with 0.25 M HCl (15 ml), water (15 ml), aqueous 1 M sodium bicarbonate, water (20 ml×3) and then dried over anhydrous magnesium sulphate. Evaporation of the solvent in vacuo gave an oil which was fractionated on silica-gel eluting with ethyl acetate-petrol (30:70) to give the title product as an oil (63 mg); $[\alpha]_D^{20}$ −3.6° (C, 0.55; CHCl$_3$); $v_{max}$ (CHCl$_3$) 1800, 1780 and 1680 cm$^{-1}$; n.m.r δ (CDCl$_3$) 3.07 (1H, d, J 17 Hz, 6β—CH), 3.23 (2H, d, J 8 Hz, 9—CH$_2$), 3.48 (1H, dd, J 17 Hz and J 2.5 Hz, 6α—CH), 4.53 (2H, s, CH$_2$OPh), 4.68 (1H t, J 8 Hz, 8—CH), 4.88 (1H, d, J 5 Hz, 4α—CH), 5.13 (1H, s, 3—CH), 5.53 (1H, q, 3'—CH), 5.63 (1H, d, J 2.5 Hz, 5—CH), 6.77–7.6 (8H, m, C$_6$H$_5$, NH, 2H of Ar—NO$_2$) 8.18 (2H, d, Ar—H).

EXAMPLE 4

Sodium 9-deoxy-9-thio [3'(R)phenoxyacetamido-2-oxoazetidin-4(R)-yl] clavulanate

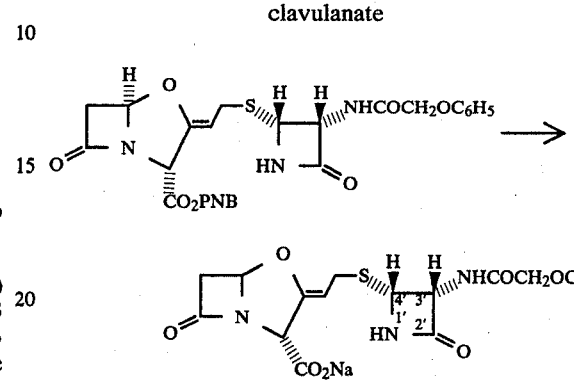

p-Nitrobenzyl 9deoxy-9-thio-[3'(R)phenoxyacetamido-2-oxoazetidin-4(R)-yl] clavulanate (0.106 g; 0.186 m.mole) in tetrahydrofuran (7 ml) was added to a prehydrogenated suspension of 10% Pd/C (110 mg) in tetrahydrofuran (8 ml) and the mixture hydrogenated at 1 atmosphere for 1 hr. After filtration through celite, a solution a sodium bicarbonate (15.6 mg) in water (1.86 ml) was added together with some more water (3 ml). The aqueous solution was washed twice with ether (5 ml) and freeze dried to give the title compound as a solid (64 mg; 75%); $v_{max}$ (KBr) 1775, 1765 and 1675 cm$^{-1}$; n.m.r δ (D$_2$O) 3.01 (1H, d, J 17 Hz, 6β—CH), 3.25 (2H, d, J 8 Hz, 9—CH$_2$), 3.53 (1H, dd, J 17 Hz and J 2.5 Hz, 6α—CH), (8—CH obscurred by HOD), 4.9 (1H, s, 3—CH), 5.03 (1H, d, J 4 Hz, 3'—CH), 5.2 (1H, d, J 4 Hz, 4'—CH), 5.67 (1H, d, J 2.5 Hz, 5—CH), 6.97–7.5 (5H, m, Ph—H).

EXAMPLE 5 p-Nitrobenzyl 9-deoxy-9-thio-(N-benzoylaminomethyl) clavulanate

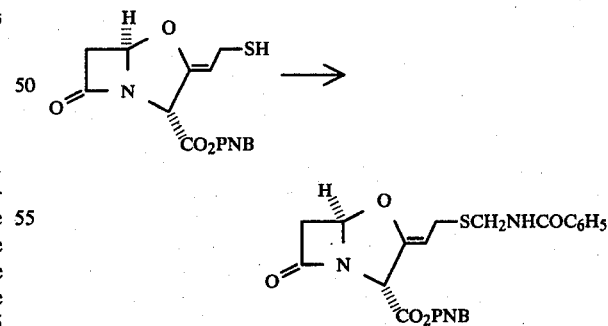

4-Nitrobenzyl (3R, 5R, Z)-2-(2-mercaptoethylidene)-clavam-3-carboxylate (0.33 g; 0.94 mmole), N-acetoxymethylbenzamide (0.18 g) and powdered zinc acetate dihydrate (30 mg) were heated under reflux in benzene (5 ml; sodium dried) for 4 hours (azetropically removing water). The cooled supernatent liquid was filtered through celite and evaporated in vacuo. The residue was fractionated on silica-gel with ethylacetate-petrol (2:3) as eluent to give the title product as an oil (0.175 g; 31%); $[\alpha]_D^{20}+18°$ (c 1.22; CHCl$_3$); $\nu_{max}$(CHCl$_3$) 3400, 1800, 1750, 1660 and 1605 cm$^{-1}$; n.m.r (CDCl$_3$) δ 3.02 (1H, d, J 17 Hz, 6β—C$\underline{H}$), 3.34 (1H, d, 9—C$\underline{H}_2$), 3.41 (1H, dd, J 17 Hz and 2.5 Hz, 6α—C$\underline{H}$), 4.49 (2H, d, —C$\underline{H}_2$NH), 4.81 (1H, t, J 8 Hz, 8—C$\underline{H}$), 5.1 (1H, s, 3—C$\underline{H}$), 5.25 (2H, s, —CO$_2$C$\underline{H}_2$), 5.61 (1H, d, J 2.5 Hz, 5—C$\underline{H}$), 7.3–8.3 (9H, m, Ar—$\underline{H}$).

EXAMPLE 6

Sodium 9-deoxy-9-thio (N-benzoylaminomethyl) clavulanate

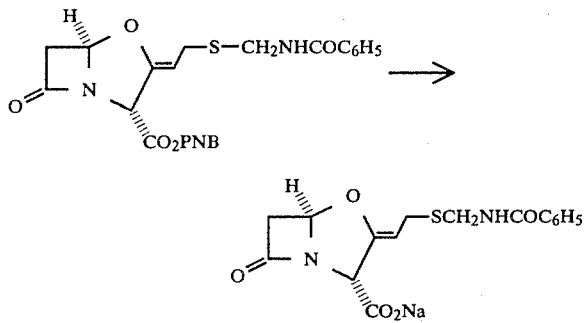

P-Nitrobenzyl 9-deoxy-9-thio (n-benzoylamino)-methyl clavulanate (0.173 g; 0.358 mmole) in tetrahydrofuran (5 ml) was added to a prehydrogenated suspension of 10% Pd/C (0.175 g) in tetrahydrofuran (7 ml) and the mixture hydrogenated at 1 atmosphere for 1.25 hours. After filtration through celite a solution of sodium bicarbonate (23.5 mg) in water (3.6 ml) was added together with more water (2 ml). The aqueous solution was washed twice with ether (10 ml) and freeze dried to give the title compound as a solid (75 mg; 57%); $\nu_{max}$ (KBr) 1780 and 1620 cm$^{-1}$; n.m.r δ (D$_2$O) 2.98 (1H, d, J 17 Hz, 6β—C$\underline{H}$), 3.43 (2H, d, 9—C$\underline{H}_2$), 3.49 (1H, dd, J 17 Hz and 2.5 Hz, 6α—C$\underline{H}$), 4.5 (1H, s, —C$\underline{H}_2$NH), 4.87 (1H, t, J 8 Hz, 8—C$\underline{H}$), 4.89 (1H, s, 3—C$\underline{H}$), 5.54 (1H, d, J 2.5 Hz, 5—C$\underline{H}$), 7.4–7.9 (5H, m, Ar—$\underline{H}$).

EXAMPLE 7 p-Nitrobenzyl 9-(2-oxopyrrolidin-1-ylmethylthio)-9-deoxyclavulanate

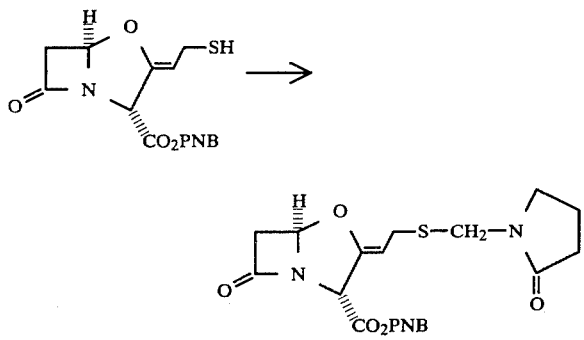

2-Pyrrolidin-2-one (1.52 ml, 20 m mole) in dimethoxyethane (15 ml) was treated with paraformaldehyde (0.66 g; 1:1 equivalents) and a catalytic amount of potassium carbonate. The mixture was heated at reflux until a clear solution was obtained and the reflux maintained for a further ½ hr. The solution was cooled and treated with 2,6-Lutidine (2.32 ml) and finally thionyl chloride (1 equivalent) at 0°–5° and the solution stirred at this temperature for 5 min. The mixture was filtered and the solvent was evaporated from the filtrate to give 1-chloromethylpyrrolidin-2-one as a yellow oil. The oil (4.6 m mole) was dissolved in dimethylformamide (5 ml) and 4-nitrobenzyl (3R, 5R, Z)-2-(2-mercaptoethylidene)-clavam-3-carboxylate (0.764 g 2.18 m mole) and 2,6-Lutidine (0.54 ml) in dimethylformamide (5 ml) added to the solution. The mixture was stirred at room temperature overnight. The mixture was diluted with ethyl acetate (100 ml) and washed with water (2×50 ml). The solvent was dried (magnesium sulphate) and the solvent evaporated under reduced pressure to give a yellow gum. Chromatography on silica-gel using ethyl acetate as eluent gave the title compound as a colourless gum (0.591 g; 61%) $\nu_{max}$ (CHCl$_3$) 1800, 1730, 1680, 1600 and 1520 cm$^{-1}$; δ(CDCl$_3$). 1.9–2.5 (4H,m) 3.0–3.6 (6H,m,6—C$\underline{H}_2$, 9—C$\underline{H}_2$, and ring—C$\underline{H}_2$), 4.34 (2H,S), 4.8 (1H,t,J7H2,8—C$\underline{H}$), 5.1 (1H,S—3C$\underline{H}$), 5.3 (2H,S,Ar—C$\underline{H}$), 5.69 (1H,d,J2.5H$_2$, 5—CH), 7.52 and 8.23 (4H, 2d, Ar—$\underline{H}$).

EXAMPLE 8

Sodium 9-(2-oxopyrrolidin-1-ylmethylthio)-9-deoxyclavulate

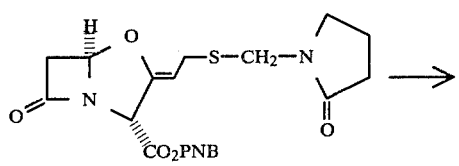

p-Nitrobenzyl-9-(2-oxopyrrolidin-1-ylmethylthio)-9-deoxyclavulanate (265 mg; 0.593 m mole) was dissolved in tetrahydrofuran and the solution was shaken with prehydrogenated 10% Pd./C (0.265 g.) under 1 atmosphere of hydrogen for 1 hour. The catalyst was removed by filtration and a solution of sodium bicarbonate (50 mg) in water (5.9 ml) was added together with more water (10 ml) and the tetrahydrofuran evaporated. The aqueous solution was washed with ether (2×10 ml), the ether evaporated, the solution adjusted to pH7 using 0.1 M HCl and the aqueous solution freeze-dried to give the title compound (74 mg.) $\nu_{max}$ (kBr) 1785 and 1620 cm.$^{-1}$; δ(D$_2$O) 1.85–2.6 (4H,m), 3.1–3.7 (6H,m), 4.44 (2H,S), 3—C$\underline{H}$ and 8—C$\underline{H}$ obscured by HOD 5–72 (1H,d,J2–5 Hz, 5—CH).

EXAMPLE 9 p-Nitrobenzyl 9-(2-oxopyrrolidin-1-ylmethylsulphonyl)-9-deoxy-clavulanate

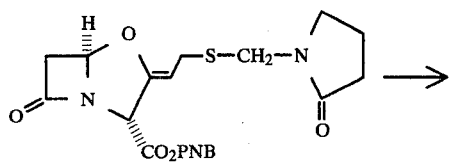

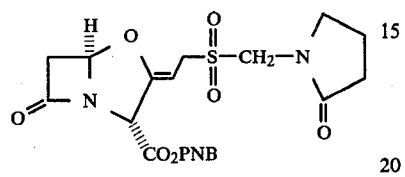

p-Nitrobenzyl-9-(2'-oxopyrrolidin-1'-ylmethylthio)-9-deoxyclavulanate (296 mg, 0.662 m mole) in dry methylene dichloride (25 ml) was cooled in an ice-bath (0°–5°) and treated dropwise with stirring with a solution of m-chloroperbenzoic acid (0.258 g, 2.25 equivalents) in dry dichloromethane (10 ml). After addition was complete the solution was stirred at 0°–5° for a further 1 hour. The reaction mixture was diluted with dichloromethane (50 ml) and washed with water (50 ml). The organic solution was further washed with aqueous 1N sodium bicarbonate, water and finally brine. The solution was dried over anhydrous magnesium sulphate and evaporated. The product was isolated from the residue by column chromatography using ethyl acetate/petrol b.p.60°–80°) (1:4) as eluent. The title compound was thus obtained as a colourless gum (136 mg), $v_{max}$ (CHCl$_3$) 1810, 1760, 1700, 1610 and 1520 cm.$^{-1}$; δ(CDCl$_3$) 1.98–2.55 (4H, m), 3.16 (1H,d,J17 Hz, 6β—C$\underline{H}$), 3.51 (1H, dd, J17 and 2.5 Hz, 6α—C$\underline{H}$), 3.56–3.9 (4H,m), 4.44 (2H,S), 4.9 (1H, t,J7 Hz, 8—C$\underline{H}$), 5.2 (1H, S, 3—C$\underline{H}$), 5.3 (2H, S, Ar—C$\underline{H}_2$), 5.76 (1H, d, J2.5 Hz, 5—C$\underline{H}$), 7.55 and 8.23 (4H, 2d, Ar—$\underline{H}$).

EXAMPLE 10

Sodium 9-(2-oxopyrrolidin-1-ylmethylsulphonyl)-9-deoxy-clavulanate

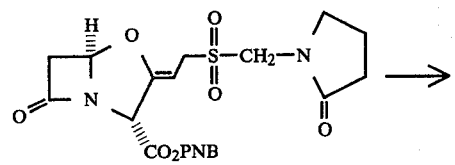

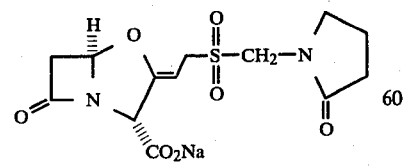

A solution of p-nitrobenzyl-9-(2-oxopyrrolidin-1'-ylmethylsuphonyl) clavulanate (136 mg, 0.284 m mole) in tetrahydrofuran (15 ml) was shaken with 10% palladium-on-charcoal (136 mg) under 1 atmosphere of hydrogen at room temperature for 1 hour. The solution was filtered through celite and the filtrate heated with a solution of sodium bicarbonate (23.8 mg) in water (2.4 ml) and a further 10 ml of water and the tetrahydrofuran evaporated. The aqueous solution was washed twice with ether (10 ml), the ether evaporated, the solution adjusted to pH7 with 0.1 MHCl and freeze-dried to give the title compound (80 mg, 77%), $v_{max}$ 1790, 1690 and 1620 cm$^{-1}$; δ(D$_2$O) 1.76–2.5 (4H,M), 3.0 (1H, d, J17 Hz, 6β—C$\underline{H}$), 3.46 (1H, dd, J17 Hz and 2.5 Hz, 6α—C$\underline{H}$) 3.45–3.7 (2H,m), 3.92 (2H,d, 9—CH$_2$), 4.68 (2H,S), 4.92 (1H,S,3—C$\underline{H}$), 5.69 (1H, d, J2–5 Hz, 5—C$\underline{H}$).

EXAMPLE 11 p-Nitrobenzyl 9-(1-formamidoethylthio)-9-deoxyclavulanate

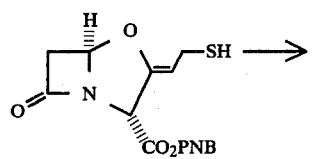

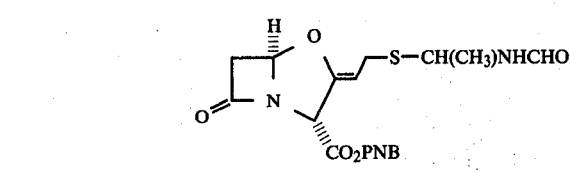

N-(1-Acetoxyethyl) formamide (0.393 g, 3 m mole) and 4-nitrobenzyl (3R, 5R, Z)-2-(2-mercaptoethylidene)-clavam-3-carboxylate (1.13 g, 3.28 m mole) were dissolved in dry benzene (25 ml). Finely powdered zinc acetate dihydrate (60 mg) was added to the solution and the mixture was stirred and refluxed with azeotropic removal of water for 2½ hours. The mixture was cooled, filtered, and evaporated to give a yellow gum. The gum was chromatographed on silica-gel using ethyl acetate-petrol (b.p. 60°–80°) (1:3) as eluent to give the title compound as a colourless gum (0.314 g; 23%), $[α]_D^{20}$+21.9° (C, 3.14; CHCl$_3$); $v_{max}$ (CHCl$_3$) 1800, 1760, 1690, 1520 and 1340 cm.$^{-1}$; δ (CDCl$_3$) 1.41 (3H, d, —CH$_3$), 2.9–3.66 (4H,m,6—C$\underline{H}_2$ and 9—C$\underline{H}_2$), 4.76 (1H,t,8—C$\underline{H}$), 5.11 (1H,S, 3—C$\underline{H}$), 5.2 (2H,S, —CO$_2$ C$\underline{H}_2$), 5.25–5.5 (1H, m, —C$\underline{H}$ CH$_3$), 5.6–5.9 (2H,m, 5—C$\underline{H}$ and —N$\underline{H}$), 7.52 and 8.24 (4H, 2d, Ar—$\underline{H}$), 8.13 (1H, S, —C$\underline{H}$O).

EXAMPLE 12 p-Nitrobenzyl 9-(1-formamidoethylsulphonyl)-9-deoxyclavulanate

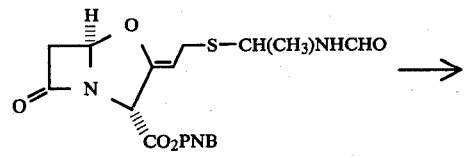

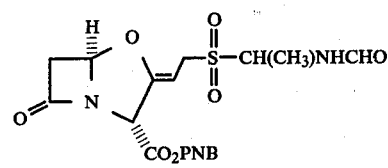

p-Nitrobenzyl 9-(1-formamidoethylthio)-9-deoxyclavulanate (367 mg, 0.872 m mole) was dissolved in dry methylene dichloride (20 ml) and treated with m-chloroperbenzoic acid (2.25 equivalents) dissolved in methylene dichloride (10 ml) at 0°. The solution was stirred at 0°-5° for 1 hour and then washed successively with water, 1N-aqueous sodium bicarbonate, and water. The organic layer was dried over anhydrous magnesium sulphate and evaporated to yield after crystallisation from ethylacetate-petrol a white solid (105 mg) $v_{max}$ (nujol mull) 3300, 1795, 1750 and 1660 cm.$^{-1}$; δ (CDCl$_3$) 1.35 (3H, m) 2.9-3.1 (4H,m), 4.79 (1H,t,J7 Hz), 5-5.3 (1H,m), 5.34 (2H,S) 5.56 (1H,S) 5.8 (1H,m).

EXAMPLE 13

Sodium 9-(1-formamidoethylthio)-9-deoxyclavulanate

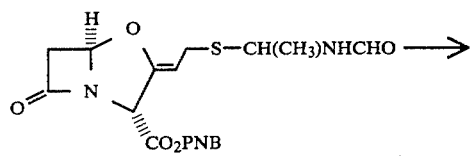

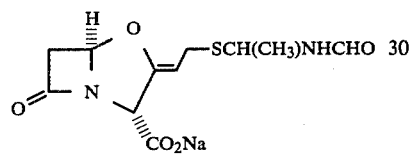

p-Nitrobenzyl 9-(1-formamido ethylthio)-9-deoxyclavulanate (314 mg; 0.75 m mole) was dissolved in dry tetrahydrofuran (10 ml) and the solution was shaken with prehydrogenated 10% palladium-on-charcoal (320 mg) under one atmosphere of hydrogen at room temperature for 1¼ hours. After filtration through celite a solution of sodium bicarbonate (62 mg) in water (6.2 ml) was added together with a further amount of water (10 ml) and the tetrahydrofuran evaporated. The aqueous solution was washed with ether (2×10 ml), the excess ether evaporated, the pH adjusted to 7 and the aqueous solution freeze-dried to give the title salt (156 mg; 68%). $v_{max}$ (KBr) 1780 and 1615 cm.$^{-1}$; δ (D$_2$O) 1.4-1.7 (3H,m,

3.13 (1H, d, J17 Hz, 6β—C$\underline{H}$), 3.3–3.75 (3H. m, 9—C$\underline{H_2}$ and 6α—C$\underline{H}$), 4.65–4.8 (1H, m, 8—C$\underline{H}$ part obscured by HOD), 5.0–5.3 (1H, m,

4.98 (1H, S, 3—C$\underline{H}$), 5.74 (1H, S—C$\underline{H}$), 8.13 (1H, m, —C$\underline{H}$O).

EXAMPLE 14

Sodium 9-(1-formamidoethylsulphonyl)-9-deoxyclavulanate

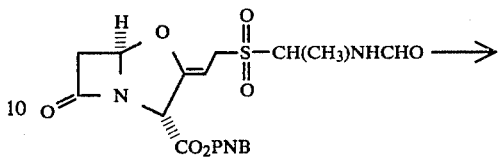

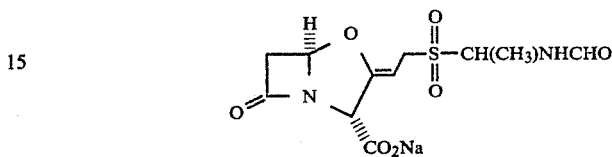

p-Nitrobenzyl 9-(1-formylamidoethylsulphonyl)-9-deoxyclavulanate (93 mg) was dissolved in dry tetrahydrofuran (25 ml) and the solution shaken with 10% palladium-on-charcoal (100 mg), under one atmosphere of hydrogen for 1 hr. The work-up as for Example 13 gave the title salt (59 mg; 85%); $v_{max}$ (KBr) 1785, 1680 and 1615 cm.$^{-1}$.

EXAMPLE 15 p-Nitrobenzyl 9-(2-oxo-1-methylazetidin-4'-yl) 9-deoxyclavulanate

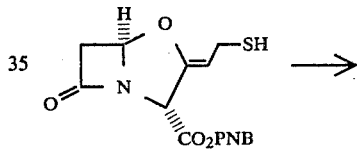

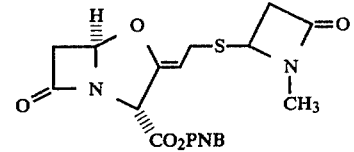

1-Methyl-3-methylthio azetidin-2-one-(0.378 g, 2.88 m mole) was dissolved in dry methylene dichloride (5 ml) and the solution was stirred and ice-cooled while a solution of chlorine in dichloromethane (1 equivalent) was added in one portion. The solution was stirred at room temperature for 2 minutes and the solvent evaporated to give 4-chloro-1-methylazetidin-2-one.

The chloride was added to a solution of 4-nitrobenzyl (3R, 5R, Z)-2-(2-mercaptoethylidene)-clavam-3-carboxylate (0.842, 2.44 m mole) and 2,6-lutidine (0.32 ml) in dimethylformamide (5 ml) and the solution stirred at room temperature overnight. Ethyl acetate (50 ml) was added and the solution was washed with 1N hydrochloric acid, water aqueous 1N sodium bicarbonate and finally water. The solution was dried (magnesium sulphate) and the solvent was evaporated to yield a yellow gum. The gum was chromatographed on silica-gel using 1:3 ethylacetate-petrol as eluent to afford the title compound (83 mg) $[α]_D^{20}$+9.75 (C, 0.83; CHCl$_3$); $v_{max}$ (CHCl$_3$) 1805, 1760 and 1520 cm.$^{-1}$; δ (CDCl$_3$) 2.75 (3H, S, N—C$\underline{H_3}$), 2.8–3.8 (6H,m), 4.5–4.9 (2H,m), 5.1

(1H,S,3—C$\underline{H}$), 5.3 (2H,S,Ar—C$\underline{H}_2$); 5.71 (1H,d,J2.5 Hz, 5—C$\underline{H}$), 7.42 and 8.23 (4H,2d,Ar—$\underline{H}$).

EXAMPLE 16

Sodium 9-(2-Oxo-1-methylazetidin-4'-yl) 9-deoxyclavulanate

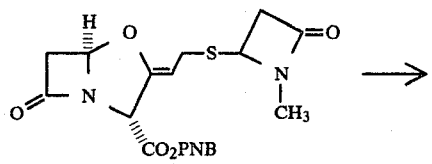

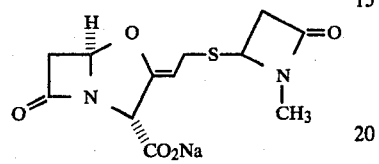

p-Nitrobenzyl 9-(2-oxo-1-methylazetidin-4-yl) 9-deoxyclavulanate (83 mg) was dissolved in dry tetrahydrofuran (5 ml) and the solution was shaken with prehydrogenated 10% palladium-on-charcoal (85 mg) under one atmosphere of hydrogen at room temperature for 1 hr. After filtration through celite a solution of bicarbonate (1 equiv) in water (2 ml) was added together with a further amount of water (10 ml) and the tetrahydrofuran evaporated. The aqueous solution was washed with ether (2×10 ml), the excess ether evaporated, the pH adjusted to 7 with 0.1 MHCl, and the aqueous solution freeze-dried to give the title salt (30 mg). $\nu_{max}$ (KBr) 1785, 1740 and 1615 cm.$^{-1}$;

EXAMPLE 17 p-Nitrobenzyl-9-(acetamidomethylthio)-9-deoxyclavulanate

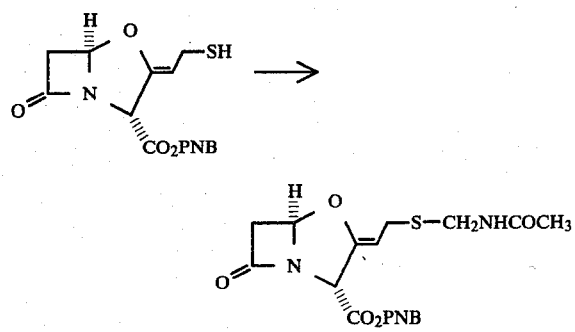

A solution of 4-nitrobenzyl (3R, 5R, Z)-2-(2-mercaptoethylidene)-clavam-3-carboxylate (0.959 g) 2.74 m mole) and acetamidomethyl acetate (0.364 g) in benzene (25 ml) containing zinc acetate dihydrate (60 mg) was refluxed using a Dean and Stark water separator for 2½ hours. The solution was cooled and filtered, and the solvent was evaporated under reduced pressure. The product was isolated from the residue by column chromatography or silica-gel using ethylacetate-petrol (b.p.60°–80°) 1:3 as eluent. The title compound was thus obtained as an oil (0.149 g.)-[α]$_D^{20}$= +3.52° [C 1.42; CHCl$_3$]; $\nu_{max}$ (CHCl$_3$) 1800, 1750, 1670 and 1520 cm.$^{-1}$; δ (CHCl$_3$) 1.98 (3H,S,C$\underline{H}_3$ CO—), 3.1 (1H,d,J17 Hz, 6β—C$\underline{H}$), 3.31 (2H,d,) δ, 3.50 (1H, dd, J17 Hz and 2 Hz, 6α—CH), 4.28 (2H,d), 4.8 (1H,t,8—C$\underline{H}$), 5.13 (S,1H,3—CH), 5.3 (2H,S,Ar—CH$_2$), 5.7 (1H, d, J2–5 Hz, 5—C$\underline{H}$), 6.3 (1H,N$\underline{H}$), 7.53 and 8.21 (4H, 2d, Ar—$\underline{H}$).

EXAMPLE 18 p-Nitrobenzyl 9-(acetamidomethylsulphinyl)-9-deoxyclavulanate

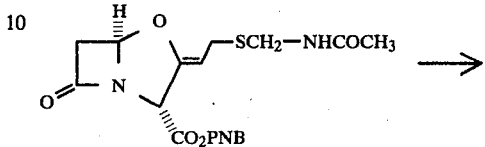

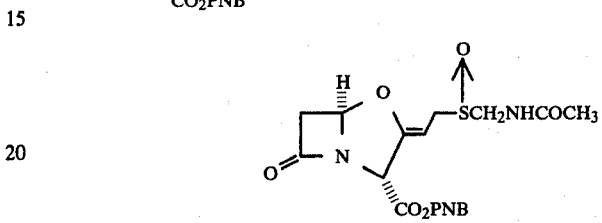

p-Nitrobenzyl 9-(acetamidomethylthio)-9-deoxyclavulanate (206 mg, 0.5 m mole) was dissolved in methylene dichloride (15 ml) and treated with m-chloroperbenzoic acid (85 mg, 1 equivalent) at 0° C. The solution was stirred at 0°–5° for 1 hr. and washed with water, 3% aqueous sodium bicarbonate solution, water, and dried over anhydrous magnesium sulphate. The solvent was evaporated and the residue chromatographed on silica-gel to yield the title product as a mixture of R and S Sulphoxides (96 mg) [α]$_D^{20}$=6.15° (C, 0.96; CHCl$_3$); $\nu_{max}$(CHCl$_3$) 1800, 1750 and 1680 cm.$^{-1}$; δ (CDCl$_3$) 2.06-(3H,S,CH$_3$CO), 2.95–3.7 (4H,6α+β—C$\underline{H}$ and 9—C$\underline{H}_2$), 4–4.15 (2H,m, —C$\underline{H}_2$) 4.71 (1H,t,J7 Hz, 8—C$\underline{H}$), 5.2 (1H, S, 3C$\underline{H}$), 5.30 (2H, 5, Ar—C$\underline{H}_2$), 5.75 (1H,m,5—C$\underline{H}$) 7.55 and 8.23 (4H, 2d, Ar—$\underline{H}$).

EXAMPLE 19 p-Nitrobenzyl 9-(acetamidomethylsulphonyl)-9-deoxyclavulanate

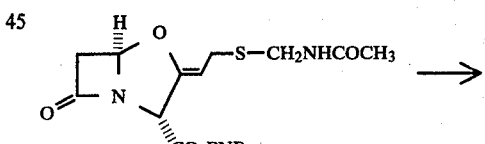

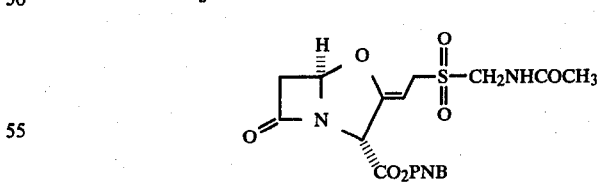

-Nitrobenzyl-9-(acetamidomethylthio)-9-deoxyclavulanate (0.244 g, 0.532 m mole) in dry methylene chloride (15 ml) was cooled in an ice-bath (0°–5°) and treated dropwise with stirring with a solution of m-chloroperbenzoic acid (2.25 equivalents) in dry dichloromethane (10 ml). After addition was complete the solution was stirred at 0°–5° for a further 1 hr. The reaction mixture was diluted with dichloromethane (50 ml) and washed with water (50 ml). The organic layer was further washed with aqueous 1N sodium bicarbonate, water and finally brine. The solution was dried over anhydrous magnesium sulphate and evaporated. The product was isolated from the residue by column chromatography using ethyl acetate as eluent. The title compound was obtained as a colourless gum (97 mg). $[\alpha]_D^{20} = +3.51$ [C 0.97;CHCl$_3$]; $\nu_{max}$ (CHCl$_3$) 1805, 1760 and 1695 cm.$^{-1}$; δ (CHCl$_3$) 1.94 (3H,S,C$\underline{H}$$_3$CO), 3.16 (1H,d,J17 Hz, 6β—C$\underline{H}$), 3.15–3.95 (3H, m, 6α—C$\underline{H}$ and 9—C$\underline{H}$$_2$), 4.4–4.6 (2H,m), 4.84 (1H,t,J7 Hz, 8 C$\underline{H}$), 5.38 (24,S,Ar—C$\underline{H}$$_2$), 5.57 (1H,S,3—CH), 5.80 (1H,d,J2–5 Hz,5—C$\underline{H}$), 7.26 and 8.24 (4H, 2d, Ar—$\underline{H}$), 8.92 (1H, br.t, N$\underline{H}$).

EXAMPLE 20

Sodium 9-(acetamidomethylthio)-9-deoxyclavulanate

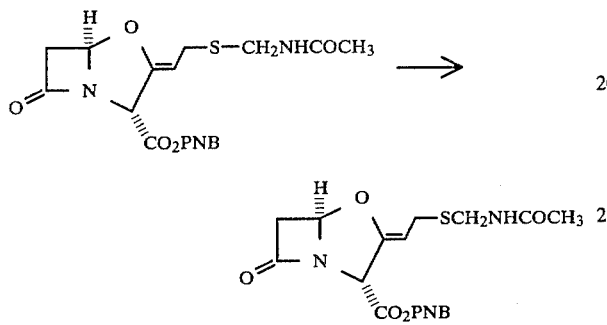

p-Nitrobenzyl 9-(acetamidomethylthio)-9-deoxyclavulanate (142 mg) was dissolved in dry tetrahydrofuran (5 ml) and the solution was shaken with prehydrogenated 10% palladium-on-charcoal (145 mg) under one atmosphere of hydrogen at room temperature for 1 hr. After filtration through celite a solution of sodium bicarbonate (28.3 mg) in water (3.3 ml) was added together with a further amount of water (10 ml) and the tetrahydrofuran evaporated. The aqueous solution was washed with ether (2×10 ml), the excess ether evaporated, the pH adjusted to 7 with 0.1 MHCl and the aqueous solution was freeze dried to give the title salt (57 mg) $\nu_{max}$(KBr) 1785 and 1640 cm.$^{-1}$; δD$_2$O 1.98 (3H,S,C$\underline{H}$$_3$CO), 3.09 (1H,d,J17 Hz, 6β—C$\underline{H}$), 3.34 (2H, S—C$\underline{H}$$_2$), 3.56 (1H,dd,J17 and 2.5 Hz, 6α—C$\underline{H}$), 4.24 (2H,d), 4.93 (1H,S,3—C$\underline{H}$), 5.71 (1H, d, J2.5 Hz, 5—C$\underline{H}$).

EXAMPLE 21

Sodium 9-(acetamidomethylsulphinyl)-9-deoxyclavulanate

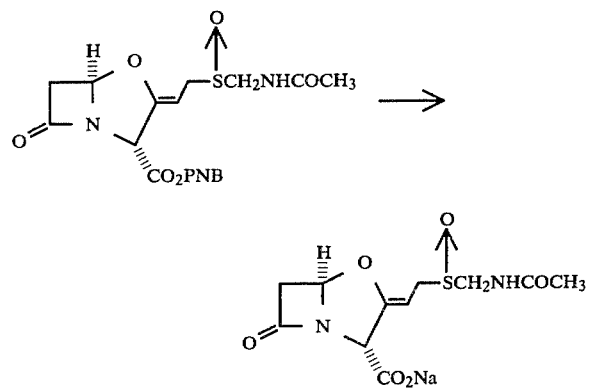

A solution of p-nitrobenzyl-9-(acetamidomethylsulphinyl)-9-deoxyclavulanate (96 mg) in dry tetrahydrofuran (10 ml) was shaken with 10% palladium-on-charcoal (100 mg) under 1 atmosphere of hydrogen for 1 hr. The solution was filtered through celite and treated with a solution of sodium bicarbonate (1 equivalent) in water (5 ml) and the tetrahydrofuran evaporated. The aqueous phase was washed twice with ether (10 ml), the ether removed, the pH adjusted to pH 7 with O—1N HCl and the solution freeze-dried to give the title salt (60 mg; 84%). $\nu_{max}$(KBr) 1785 and 1620 cm.$^{-1}$; δ(D$_2$O) 1.98 (3H,S,C$\underline{H}$$_3$CO), 3.02 (1H,d,J17 Hz, 6β—C$\underline{H}$), 3.5 (1H,dd, J17 and 2.5 Hz, 6α—C$\underline{H}$) 3.61 (2H,d,J7 Hz,9—C$\underline{H}$$_2$), 5.68 (1H, d,J2.5 Hz,5—C$\underline{H}$).

EXAMPLE 22

Sodium 9-(acetamidomethylsuphonyl)-9-deoxyclavulanate

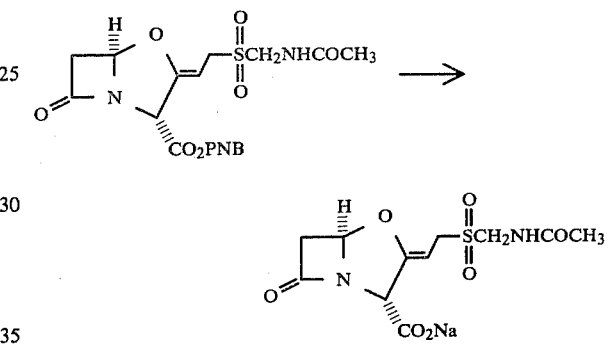

p-Nitrobenzyl 9-(acetamidomethylsulphonyl)-9-deoxyclavulanate (97 mg; 0.214 m mole) was dissolved in tetrahydrofuran (5 ml) and the solution was shaken with 10% palladium-on-charcoal (97 mg) suspended in tetrahydrofuran (10 ml) under one atmosphere of hydrogen at room temperature for 1 hr. The solution was filtered through celite and the filtrate treated with a solution of sodium bicarbonate (1 equivalent) in water (5 ml) and further amount of water (5 ml) and the tetrahydrofuran evaporated. The aqueous solution was washed twice with ether (2×10 ml), the ether evaporated and the solution adjusted to pH 7 with 0.1 MHCl and freeze-dried to give the title salt (46 mg, 63%) $\nu_{max}$(KBr) 1785, 1680, 1620 and 1540 cm.$^{-1}$; δ(D$_2$O) 2.03 (3H,S,C$\underline{H}$$_3$CO), 3.08 (1H,d,J17 Hz, 6β—C$\underline{H}$), 3.52 (1H,dd,J17 and 2.5 Hz, 6α—C$\underline{H}$), 3.95 (2H,d,J7 Hz,9—C$\underline{H}$$_2$), 5.74 (1H, d,J2.5 Hz,5—C$\underline{H}$).

EXAMPLE 23 p-Nitrobenzyl 9-deoxy-9-sulphonyl(azetidin-2'-on-4'-yl)clavulanate

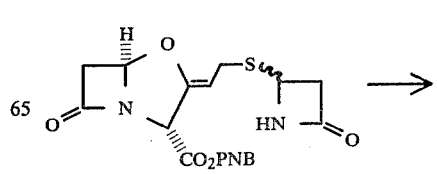

-continued

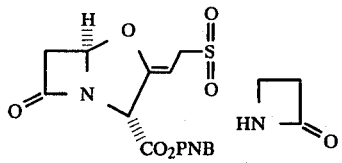

A solution o p-nitrobenzyl-9-deoxy-9-thio(azetidin-2'-on-4'-yl)clavulanate (134 mg) in dry methylene dichloride (10 ml) was cooled in an ice-bath (0°–5°) and treated dropwise with stirring with a solution of m-chloroperbenzoic acid (100 mg) in dry methylene dichloride (10 ml). After addition was complete the solution was stirred at 0°–5° for a further 2 hours. The reaction mixture was diluted with dichloromethane (30 ml) and washed with water (30 ml). The organic layer was further washed with aqueous 1N sodium bicarbonate, water and finally brine. The solution was dried over anhydrous magnesium sulphate and evaporated. The product was isolated from the residue by column chromatography on silica-gel using ethyl acetate-petrol (b.p.—60°–80°) 1:1 as eluent. The title compound was obtained as a colourless foam (85 mg). $\nu_{max}$(CHCl$_3$) 1800, 1760, 1610 and 1520 cm.$^{-1}$; $\delta$(CDCl$_3$) 3.14 (1H,d,J17 Hz, 6$\beta$—C$\underline{H}$), 3.25 (2H,m,3'–C$\underline{H}_2$), 3.56 (1H,dd,J17 Hz and 2.5 Hz, 6$\alpha$—C$\underline{H}$), 3.90 (2H,m,9—C$\underline{H}_2$), 4.5–5.0 (m,3H), 5.3 (2H,S,Ar—C$\underline{H}_2$) 5.80 (1H,d,J2.5 Hz, 5—C$\underline{H}$), 7.25 (1H,br.s, N$\underline{H}$), 7.52 and 8.21 (4,2d,Ar—$\underline{H}$).

EXAMPLE 24

Sodium 9-deoxy-9-sulphonyl(azetidin-2-on-4-yl)clavulanate

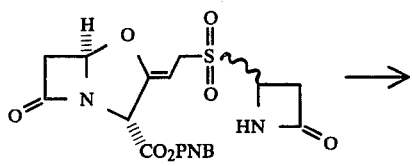

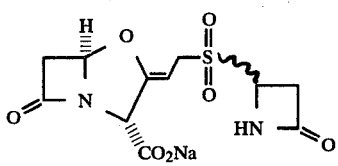

p-Nitrobenzyl 9-deoxy-9-sulphonyl(azetidin-2-on-4-yl)clavulanate (4.5 mg) was dissolved in tetrahydrofuran (10 ml) and the solution shaken with 10%-palladium-on-charcoal (50 mg) under 1 atmosphere of hydrogen for 1 hr. The catalyst was removed by filtration and the solution treated with sodium bicarbonate (1 equivalent) in water (5 ml) and the tetrahydrofuran evaporated. The aqueous phase was washed with ether (2×10 ml), the ether evaporated and the pH adjusted to 7 with 0.1 M HCl. The aqueous layer was freeze-dried to provide the title salt (16 mg; 43%), $\nu_{max}$(KBr) 1780, 1690 and 1620 cm.$^{-1}$.

EXAMPLE 25 p-Nitrobenzyl 9-(N-formyl-N-methylaminomethylthio)-9-deoxyclavulanate

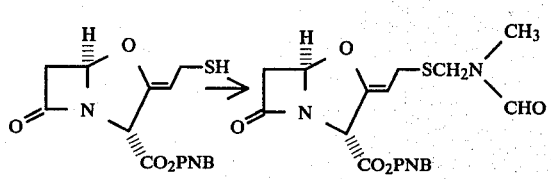

N-methylformamide (5.91 g) and paraformaldehyde (3.0 g) were heated together at 100° for 2 hrs. in the presence of a catalytic amount of potassium carbonate. Low boiling constituents were removed to leave N-methyl-N-hydroxymethylformamide (8 g).

N-methyl-N-hydroxymethylformamide (338 mg) was dissolved in dimethoxyethane (10 ml) and the solution cooled to 0°. The solution was treated with 2, 6-lutidine (0.47 ml) and then thionylchloride (0.29 ml) was added dropwise with stirring. Stirring was continued at 5° for 1 hr. after which time the solution was filtered and evaporated to leave N-methyl-N-chloromethylformamide as a pale yellow oil. The oil was dissolved in dimethylformamide (10 ml) and 4-nitrobenzyl (3R, 5R, Z)-2-(2-mercaptoethylidene)-clavam-3-carboxylate (1.4 g) and 2,6,-Lutidine (0.46 ml) in dimethylformamide (10 ml) added to the solution. The mixture was stirred at room temperature overnight and diluted with excess ethyl acetate. The organic solution was washed with water (2×50 ml), dried over anhydrous magnesium sulphate and the solvent evaporated to give a yellow gum. Chromatography on silica-gel using ethyl acetate-petrol as eluent gave the title compound as a colourless oil (314 mg 23%) $[\alpha]_D^{20}=+24.56$ [C,1.51; CHCl$_3$]$\nu_{max}$(CHCl$_3$) 1800, 1750, 1670 and 1520 cm.$^{-1}$; $\delta$(CDCl$_3$) 2.87 and 2.96 (3H,2S,N—C$\underline{H}_3$), 3–3.7 (4H,6—C$\underline{H}_2$ and 9—C$\underline{H}_2$), 4.24 and 4.42 (2H, 2S, —C$\underline{H}_2$—N), 4.5–4.95 (1H,m,8—C$\underline{H}$), 5.13 and 5.15 (1H, 2S, 3—C$\underline{H}$), 5.30 (2H, S, Ar—C$\underline{H}_2$), 5.7 (1H,m,5—C$\underline{H}$), 7.25 and 8.22 (4H, 2d, Ar—$\underline{H}$), 7.94 and 8.06 (1H, 2S, N—C$\underline{H}$O).

EXAMPLE 26 p-Nitrobenzyl-9-(N-formyl-N-methylaminomethylsulphonyl)-9-deoxyclavulanate

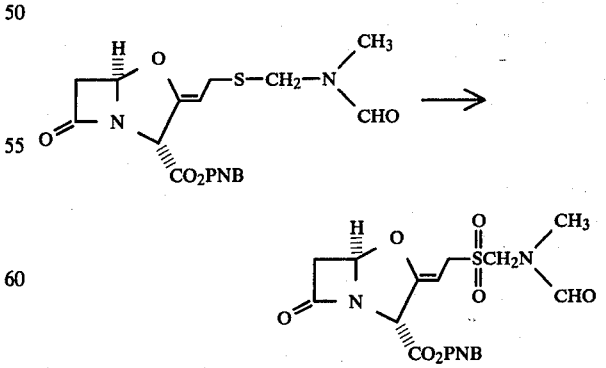

p-Nitrobenzyl 9-(N-formyl-N-methylaminomethylthio)-9-deoxyclavulanate (0.194 g) was dissolved in dry dichloromethane (15 ml) and treated with m-chloroperbenzoic acid (2.25 equivalents) at 0°. The solution was stirred at 0°-5° for 1 hr. and then washed successively with water, 1N aqueous sodiumbicarbonate, water and finally brine. The organic layer was dried over anhydrous magnesium sulphate and evaporated to leave a gum. Chromatography on silica-gel using ethyl acetate-petrol as eluent gave the title ester as a colourless gum (0.101 g; 48%) $[\alpha]_D^{20} = +5.24$ [C, 1.01; CHCl$_3$]$\nu_{max}$(CHCl$_3$) 1800, 1750, 1730 (Sh), 1680 and 1520 cm.$^{-1}$; $\delta$(CDCl$_3$) 3.06 and 3.2 (3H, 2S, N—C$\underline{H}_3$), 3.3-4.2 (4H, 6—C$\underline{H}_2$ and 9—C$\underline{H}_2$), 4.42 and 4.52 (2H, 2S, —C$\underline{H}_2$N), 4.88 (1H, dt, J1 and 7 Hz, 8—C$\underline{H}$), 5.22 (1H, S, —3—C$\underline{H}$), 5.30 (2H, S, Ar—C$\underline{H}_2$), 5.75 (1H, d, J2-5 HZ, 5—C$\underline{H}$), 7.22 and 8.22 (4H, 2d, Ar—$\underline{H}$), 8.04 and 8.11 (1H, 2S, N—C$\underline{H}$O).

EXAMPLE 27

Sodium-9(N-formyl-N-methylaminomethlthio)-9-deoxyclavulanate

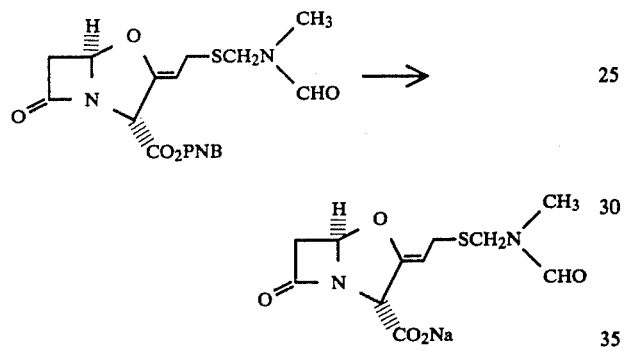

p-Nitrobenzyl-9-(N-formyl-N-methlaminomethylthio)-9-deoxyclavulanate (151 mg) was dissolved in dry tetrahydrofuran (8 ml), added to a prehydrogenated suspension of 10% palladium-on-charcoal (150 mg) in tetrahydrofuran (8 ml) and the solution shaken under 1 atmosphere of hydrogen for 1 hr. The catalyst was removed by filtration and the solution treated with sodium bicarbonate (1 equivalent) in water (10 ml) and the tetrahydrofuran evaporated. The aqueous phase was washed with ether (2×20 ml), the ether evaporated and the pH adjusted to 7 with 0.1 M HCl. The aqueous solution was freeze-dried to give the title salt (71 mg) $\nu_{max}$(KBr) 1785, 1660 and 1615 cm.$^{-1}$; $\delta$(D$_2$O) 2.83 (3H, S, N—C$\underline{H}_3$), 2.9-3.70 (4H, 9—C$\underline{H}_2$ and 6—C$\underline{H}_2$), 4.40 (2H, S, —C$\underline{H}_2$N), 4.88 (1H, t, J7 Hz, 8—C$\underline{H}$), 5.67 (1H, d, J2.5 Hz, 5—C$\underline{H}$), 7.94 (1H, S. N—C$\underline{H}$O).

EXAMPLE 28

Sodium 9-(N-formyl-N-methylaminomethylsulphonyl)-9-deoxyclavulanate

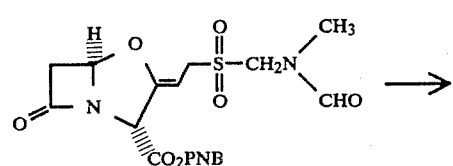

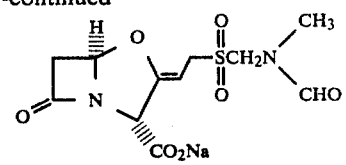

p-Nitrobenzyl 9-(N-formyl-N-methylaminomethylsulphonyl)-9-deoxyclavulanate (101 mg) was dissolved in dry tetrahydrofuran (15 ml) and the solution shaken with 10% palladium-on-charcoal (100 mg) under 1 atmosphere of hydrogen for 1 hr. The work-up procedure was as for Example 27 and gave the title salt (53 mg.), $\nu_{max}$(KBr) 1785, 1670 and 1620 cm.$^{-1}$; $\delta$(D$_2$O) 3.03 and 3.18 (3H, 2S, N—C$\underline{H}_3$), 3.3-4.3 (4H, 9—C$\underline{H}_2$, 6—C$\underline{H}_2$), 4.83 and 4.87 (2H, 2S, —C$\underline{H}_2$N), 5.14 (1H, S, 3—C$\underline{H}$), 5.77 (1H, 5—C$\underline{H}$), 8.10 and 8.15 (1H, 2S, N—C$\underline{H}$O).

EXAMPLE 29

Composition a. Amoxycillin trihydrate (250 mg) and the compound of Example 21 (100 mg) are filled into a two part hard gelatin capsule. This is suitable for administration by mouth.

b. Sodium amoxycillin (250 mg) and the compound of Example 10 (50 mg) are sealed into a glass vial. This is suitable for reconstitution with water for injection BP (1.5 ml) to form an injectable solution.

DEMONSTRATION 1

Synergistic Activity

The minimum inhibitory concentration (MIC) of ampicillin alone or in the presence of certain compounds of the invention was determined for several strains of bacteria. The results are shown below.

| Compound of Example No | Conc. (μg/ml) | MIC Ampicillin (μg/ml) | | | |
|---|---|---|---|---|---|
| | | Staph. Russell | Klebsiella E70 | Proteus C889 | E.coli JT39 |
| 6 | 20 | <0.1 | 12.5 | 2 | 4 |
| | 5 | <0.1 | 12.5 | 4 | 16 |
| | 1 | 0.2 | 25 | 16 | 125 |
| | 0 | 500 | 2000 | >2000 | 2000 |
| Compound alone | — | 16 | 500 | 125 | 250 |
| 2 | 20 | — | — | — | — |
| | 5 | 0.04 | 1.5 | 1 | 2 |
| | 1 | 0.3 | 6.25 | 4 | 8 |
| | 0 | 500 | 500 | 1000 | 2000 |
| Compound alone | — | 31.2 | 15 | 15 | 31.2 |

DEMONSTRATION 2

Synergistic Activity

The MIC of ampicillin alone or in the presence of certain compounds of the invention was determined for certain Gram positive and Gram negative bacteria. The results are shown below (in μg/ml):

| Compound | Inhibitor Conc. (μg/ml) | Staph. aureus Russell | Kleb. aerogenes E70 | E. coli JT39 |
|---|---|---|---|---|
| Ampicillin | — | 125–500 | 500–2000 | ≧2000 |
| Amp + Comp Ex. 2 | 5 | 0.04 | 1.5 | 2 |
| Amp + Comp Ex. 2 | 1 | 0.3 | 6.2 | 8 |
| Comp Ex. 2 alone | — | 31.2 | 16 | 31.2 |
| Amp + Comp Ex. 6 | 5 | <10.1 | 12.5 | 16 |
| Amp + Comp Ex. 6 | 1 | 0.2 | 25 | 125 |
| Comp Ex. 6 alone | — | 16 | 500 | 250 |
| Amp + Comp Ex. 20 | 5 | 0.16 | 6.2 | 4 |
| Amp + Comp Ex. 20 | 1 | 0.6 | 12.5 | 31.2 |
| Comp Ex. 20 alone | — | 4 | 62.5 | 62.5 |
| Amp + Comp Ex. 8 | 5 | 0.16 | 12.5 | 31.2 |
| Amp + Comp Ex. 8 | 1 | 0.6 | 25 | 250 |
| Comp Ex. 8 alone | — | 62.5 | 250 | 250 |
| Amp + Comp Ex. 10 | 5 | 0.08 | 3.1 | 4 |
| Amp + Comp Ex. 10 | 1 | 0.3 | 3.1 | 8 |
| Comp Ex. 10 alone | — | 31.2 | 62.5 | 62.5 |
| Amp + Comp Ex. 13 | 5 | 0.02 | 3.1 | 4 |
| Amp + Comp Ex. 13 | 1 | 0.08 | 6.2 | 16 |
| Com Ex. 13 alone | — | 16 | 62.5 | 125 |
| Amp + Comp Ex. 22 | 5 | 0.3 | 1.6 | 1 |
| Amp + Comp Ex. 22 | 1 | 0.6 | 3.1 | 4 |
| Comp Ex. 22 alone | — | 62.5 | 62.5 | 31.2 |
| Amp + Comp Ex. 21 | 5 | 0.3 | 3.1 | 4 |
| Amp + Comp Ex. 21 | 1 | 1.2 | 6.2 | 8 |
| Comp Ex. 21 alone | — | 125 | 125 | 62.5 |

DEMONSTRATION 3

In-vivo Effect

The $CD_{50}$ in mice infected intraperitoneally with *E.coli* E96 was determined. Amoxycillin and the synergists were dosed subcutaneously at 1 and 5 hours post infection. The synergists were used at 2 mg/kg.

|  | $CD_{50}$ (mg/kg × 2) |
|---|---|
| Amoxycillin alone | >1000 |
| Amoxycillin + Comp Ex. 20 | 20 |
| Amoxycillin + Comp Ex. 13 | 17 |
| Amoxycillin + Comp Ex. 24 | 25 |
| Amoxycillin + Comp Ex. 21 | 6 |
| Amoxycillin + Comp Ex. 22 | 9 |
| Amoxycillin + Comp Ex. 28 | 9 |
| Amoxycillin + Comp Ex. 10 | 8 |

These tests show that good activity is obtained.

No drug induced overt toxic effects have been observed at the therapeutic dose. The $LD_{50}$ of the compounds is typically >500 mg/kg/po.

What we claim is:

1. A compound of the formula (I):

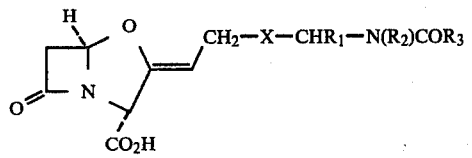

or a pharmaceutically acceptable salt or pharmaceutically acceptable ester thereof wherein $R_1$ is hydrogen, lower alkyl, phenyl, thienyl, furyl, phenyl mono-substituted by fluoro, chloro, lower alkyl or lower alkoxy, or lower alkyl mono-substituted by phenyl, thienyl, furyl, or phenyl which is itself mono-substituted by fluoro, chloro, lower alkyl or lower alkoxy, $R_2$ and $R_3$ are independently hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy, and X is S,SO or $SO_2$ and wherein lower alkyl is alkyl of 1 to 6 carbon atoms.

2. A compound according to claim 1 of the formula (II), (III), (V), (VI), (VII), or (IX):

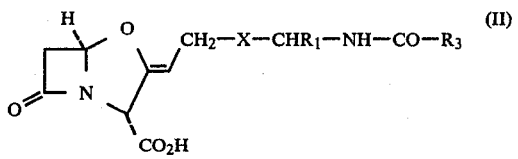

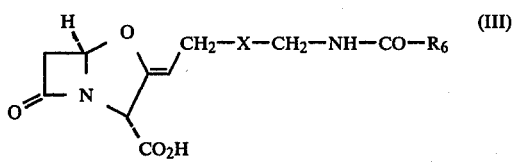

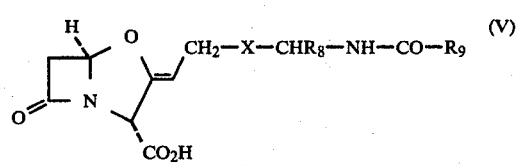

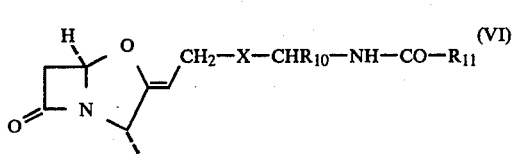

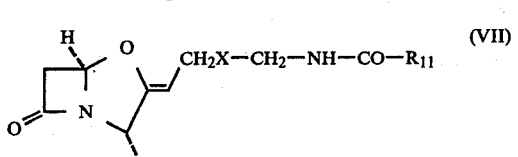

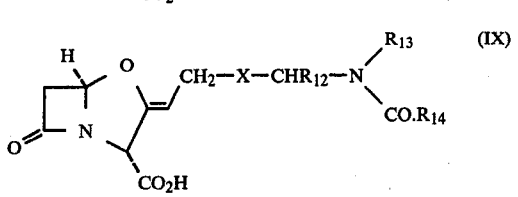

or a pharmaceutically acceptable salt thereof wherein:
(i) in relation to formula (II) $R_1$ is hydrogen and $R_3$ is hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy and X is S,SO or SO$_2$;

(ii) in relation to formula (III) R$_6$ is hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluoro, chloro, lower alkyl or lower alkoxyester, amino or aryl, and X is S,SO, or SO$_2$;

(iii) in relation to formula (V) R$_8$ is lower alkyl, phenyl, thienyl, furyl, phenyl mono-substituted by fluoro, chloro lower alkyl or lower alkoxy or lower alkyl mono-substituted by phenyl, thienyl, furyl, or phenyl which is itself mono-substituted by fluoro, chloro, lower alkyl or lower alkoxy, R$_9$ is hydrogen phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy and X is SO or SO$_2$;

(iv) in relation to formula (VI) R$_{10}$ is hydrogen or lower alkyl and R$_{11}$ is lower alkyl mono-substituted by amino or by amino and by phenyl, thienyl, furyl, phenyl mono-substituted by fluoro, chloro, lower alkyl or lower alkoxy and X is S,SO or SO$_2$;

(v) in relation to formula (VII) R$_{11}$ is alkyl of up to 4 carbon atoms mono-substituted by amino or is alkyl of up to 4 carbon atoms mono-substituted by amino and by phenyl, thienyl, furyl, phenyl mono-substituted by fluoro, chloro, lower alkyl or lower alkoxy and X is S,SO or SO$_2$; and (vi) in relation to formula (IX) R$_{12}$ is hydrogen, lower alkyl, phenyl, thienyl, furyl, phenyl mono-substituted by fluoro, chloro, lower alkyl or lower alkoxy or lower alkyl or lower alkyl mono-substituted by phenyl, thienyl, furyl, or phenyl which is itself mono-substituted by fluoro, chloro, lower alkyl or lower alkoxy lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluor, chloro, lower alkyl or lower alkoxy ester, amino or phenyl, thienyl, furyl, phenyl mono-substituted by fluoro, chloro, lower alkyl or lower alkoxy, and R$_{14}$ is lower alkyl and X is S,SO or SO$_2$.

3. A compound according to claim 1 of the formula (XIa):

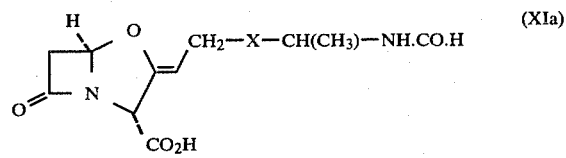

or a pharmaceutically acceptable salt thereof wherein X is S, SO or SO$_2$.

4. A compound according to claim 1 of the formula (XIb):

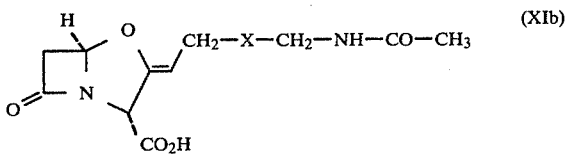

or a pharmaceutically acceptable salt thereof wherein X is S, SO or SO$_2$.

5. A compound according to claim 1 of the formula (XIV):

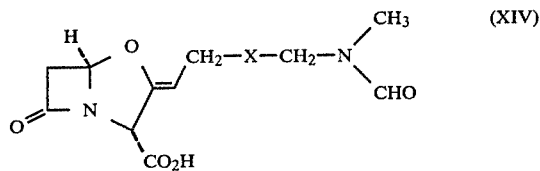

or a pharmaceutically acceptable salt thereof wherein X is S, SO or SO$_2$.

6. A compound according to claim 1 in the form of a sodium, potassium, calcium or magnesium salt.

7. A compound according to claim 1 of the formula (II), (III), (V), (VI), (VII), or (IX):

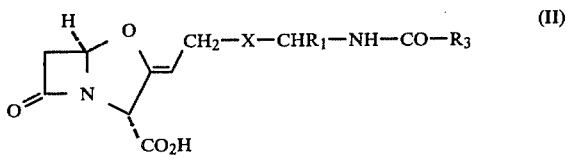

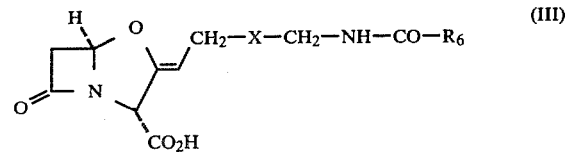

-continued

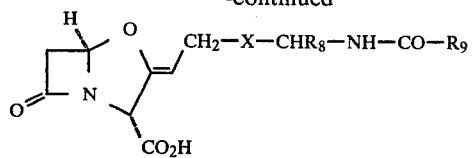 (V)

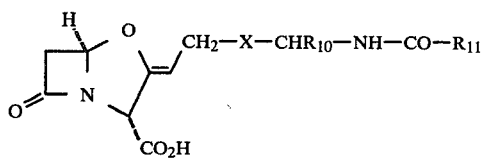 (VI)

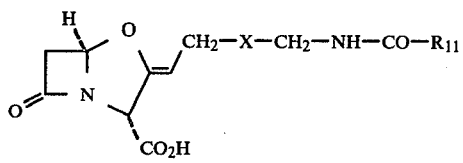 (VII)

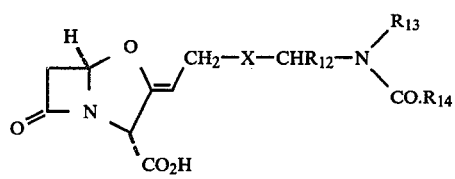 (IX)

or a pharmaceutically acceptable salt thereof wherein:

(i) in relation to formula (II) $R_1$ is hydrogen and $R_3$ is hydrogen, phenyl, thienyl, furyl, phenyl, mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy and X is S,SO or $SO_2$;

(ii) in relation to formula (III) $R_6$ is hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carbocylic acid lower alkyl ester, a carboxylic acid lower alkyl mono-substituted by phenyl, thienyl, furyl, or phenyl which is itself mono-substituted by fluoro, chloro, lower alkyl or lower alkoxyester, amino or aryl, and X is S,SO, or $SO_2$;

(iii) in relation to formula (V) $R_8$ is lower alkyl, phenyl, thienyl, furyl, phenyl mono-substituted by fluoro, chloro lower alkyl or lower alkoxy or lower alkyl mono-substituted by phenyl, thienyl, furyl, or phenyl which is itself mono-substituted by fluoro, chloro, lower alkyl or lower alkoxy, $R_9$ is hydrogen phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy and X is SO or $SO_2$;

(iv) in relation to formula (VI) $R_{10}$ is hydrogen or lower alkyl and $R_{11}$ is lower alkyl mono-substituted by amino or by amino and by phenyl, thienyl, furyl, phenyl mono-substituted by fluoro, chloro, lower alkyl or lower alkoxy and X is S, SO or $SO_2$;

(v) in relation to formula (VII) $R_{11}$ is alkyl of up to 4 carbon atoms mono-substituted by amino or alkyl of up to 4 carbon atoms mono-substituted by amino and by phenyl, thienyl, furyl, phenyl mono-substituted by fluoro, chloro, lower alkyl or lower alkoxy and X is S,SO or $SO_2$; and (vi) in relation to formula (IX) $R_{12}$ is hydrogen, lower alkyl, phenyl, thienyl, furyl, phenyl mono-substituted by fluoro, chloro, lower alkyl or lower alkoxy or lower alkyl or lower alkyl mono-substituted by phenyl, thienyl, furyl, or phenyl which is itself mono-substituted by fluoro, chloro, lower alkyl or lower alkoxy lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluor, chloro, lower alkyl or lower alkoxy ester, amino or phenyl, thienyl, furyl, phenyl mono-substituted by fluoro, chloro, lower alkyl or lower alkoxy, and $R_{14}$ is lower alkyl and X is S,SO or $SO_2$.

8. A compound according to claim 1 in the form of a pharmaceutically acceptable salt.

9. A compound according to claim 2 in the form of a sodium, potassium, calcium or magnesium salt.

10. A compound according to claim 3 in the form of a sodium, potassium, calcium or magnesium salt.

11. A compound according to claim 4 in the form of a sodium, potassium, calcium or magnesium salt.

12. A compound according to claim 8 in the form of a sodium, potassium, calcium or magnesium salt.

13. The compound according to claim 1 which is p-nitrobenzyl 9-deoxy-9-thio-(N-benzoylaminomethyl)-clavulanate.

14. The compound according to claim 1 which is sodium 9-deoxy-9-thio(N-benzoylaminomethyl)clavulanate.

15. The compound according to claim 1 which is p-nitrobenzyl 9-(1-formamidoethylthio)-9-deoxy-clavulanate.

16. The compound according to claim 1 which is p-nitrobenzyl 9-(1-formamidoethylsulphonyl)-9-deoxyclavulanate.

17. The compound according to claim 1 which is sodium 9-(1-formamidoethylthio)-9-deoxyclavulanate.

18. The compound according to claim 1 which is sodium 9-(1-formamidoethylsulphonyl)-9-deoxyclavulanate.

19. The compound according to claim 1 which is p-nitrobenzyl-9-(acetamidomethylthio)-9-deoxyclavulanate.

20. The compound according to claim 1 which is p-nitrobenzyl 9-(acetamidomethylsulphinyl)-9-deoxyclavulanate.

21. The compound according to claim 1 which is p-nitrobenzyl 9-(acetamidomethylsulphonyl)-9-deoxyclavulanate.

22. The compound according to claim 1 which is sodium 9-(acetamidomethylthio)-9-deoxyclavulanate.

23. The compound according to claim 1 which is sodium 9-(acetamidomethylsulphinyl)-9-deoxyclavulanate.

24. The compound according to claim 1 which is sodium 9-(acetamidomethylsulphonyl)-9-deoxyclavulanate.

25. The compound according to claim 1 which is p-nitrobenzyl 9-(N-formyl-N-methylaminomethylthio)-9-deoxyclavulanate.

26. The compound according to claim 1 which is p-nitrobenzyl-9-(N-formyl-N-methylaminomethylsulphonyl)-9-deoxyclavulanate.

27. The compound according to claim 1 which is sodium-9 (N-formyl-N-methylaminomethylthio)-9-deoxyclavulanate.

28. The compound according to claim 1 which is sodium 9-(N-formyl-N-methylaminomethylsulphonyl)-9-deoxyclavulanate.

29. A pharmaceutical composition useful for treating bacterial infections in mammals including humans which comprises an antibacterially effective amount of a compound of the formula (I):

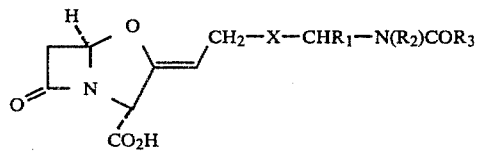

or a pharmaceutically acceptable salt or pharmaceutically acceptable ester thereof wherein Ris is hydrogen, lower alkyl, phenyl, thienyl, furyl, phenyl mono-substituted by fluoro, chloro, lower alkyl or lower alkoxy, or lower alkyl mono-substituted by phenyl, thienyl, furyl, or phenyl which is itself mono-substituted by fluoro, chloro, lower alkyl or lower alkoxy, $R_2$ and $R_3$ are independently hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mon-substituted by fluoro, chloro, lower alkyl or lower alkoxy, and X is S,SO or $SO_2$ and wherein lower alkyl is alkyl of 1 to 6 carbon atoms, in combination with a pharmaceutically acceptable carrier.

30. A composition according to claim 29 wherein the compound is of the formula (XIa):

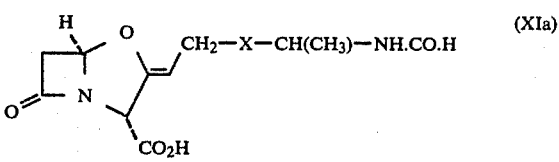

or a pharmaceutically acceptable salt thereof wherein X is S, SO or $SO_2$.

31. A composition according to claim 29 wherein the compound is of the formula (XIb):

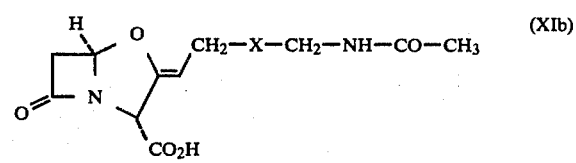

or a pharmaceutically acceptable salt thereof wherein X is S, SO or $SO_2$.

32. A composition according to claim 29 wherein the compound is of the formula (XIV):

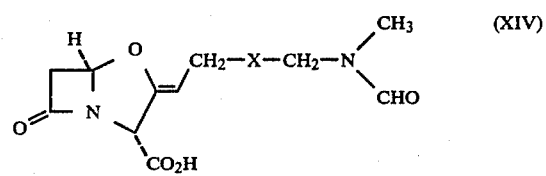

or a pharmaceutically acceptable salt thereof wherein X is S, SO or $SO_2$.

33. A composition according to claim 29 wherein the compound is in the form of a pharmaceutically acceptable salt.

34. A composition according to claim 33 wherein the salt is a sodium, potassium, calcium or magnesium salt.

35. A comosition according to claim 7 wherein the compound is in the form of a pharmaceutically acceptable salt selected from the group consisting of a sodium, potassium, calcium and magnesium salt.

36. A composition according to claim 30 wherein the compound is in the form of a pharmaceutically acceptable salt selected from the group consisting of a sodium, potassium, calcium and magnesium salt.

37. A composition according to claim 32 wherein the compound is in the form of a pharmaceutically acceptable salt selected from the group consisting of a sodium, potassium, calcium and magnesium salt.

38. A method of treating bacterial infections in mammals including humans which comprises administering to such a mammal in need thereof an antibacterially effective amount of a compound of the formula (I):

$$\text{(I)}\quad \text{structure: azetidinone fused with oxygen ring, } CH_2-X-CHR_1-N(R_2)COR_3,\ CO_2H$$

or a pharmaceutically acceptable salt or pharmaceutically acceptable ester thereof wherein $R_1$ is hydrogen, lower alkyl, phenyl, thienyl, furyl, phenyl mono-substituted by fluoro, chloro, lower alkyl or lower alkoxy, or lower alkyl mono-substituted by phenyl, thienyl, furyl, or phenyl which is itself mono-substituted by fluoro, chloro, lower alkyl or lower alkoxy, $R_2$ and $R_3$ are independently hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy, and X is S, SO or $SO_2$ and wherein lower alkyl is alkyl of 1 to 6 carbon atoms, in combination with a pharmaceutically acceptable carrier.

39. A composition according to claim 29 wherein the compound is p-nitrobenzyl 9-(1-formamidoethylthio)-9-deoxyclavulanate.

40. A composition according to claim 29 wherein the compound is p-nitrobenzyl 9-deoxy-9-thio(N-benzoylaminomethyl)clavulanate.

41. A composition according to claim 29 wherein the compound is sodium 9-deoxy-9-thio(N-benzoylaminomethyl)clavulanate.

42. A composition according to claim 29 wherein the compound is p-nitrobenzyl 9-(1-formamidoethylsulphonyl)-9-deoxyclavulanate.

43. A composition according to claim 29 wherein the compound is sodium 9-(1-formamidoethylthio)-9-deoxyclavulanate.

44. A composition according to claim 29 wherein the compound is sodium 9-(1-formamidoethylsulphonyl)-9-deoxyclavulanate.

45. A composition according to claim 29 wherein the compound is p-nitrobenzyl-9-(acetamidomethylthio)-9-deoxyclavulanate.

46. A composition according to claim 29 wherein the compound is p-nitrobenzyl 9-(acetamidomethylsulphinyl)-9-deoxyclavulanate.

47. A composition according to claim 29 wherein the compound is p-nitrobenzyl 9-(acetamidomethylsulphonyl)-9-deoxyclavulanate.

48. A composition according to claim 29 wherein the compound is sodium 9-(acetamidomethylthio)-9-deoxyclavulanate.

49. A composition according to claim 29 wherein the compound is sodium 9-(acetamidomethylsulphinyl)-9-deoxyclavulanate.

50. A composition according to claim 29 wherein the compound is sodium 9-(acetamidomethylsulphonyl)-9-deoxyclavulanate.

51. A composition according to claim 29 wherein the compound is p-nitrobenzyl 9-(N-formyl-N-methylaminomethylthio)-9-deoxyclavulanate.

52. A composition according to claim 29 wherein the compound is p-nitrobenzyl-9-(N-formyl-N-methylaminomethylsulphonyl)-9-deoxyclavulanate.

53. A composition according to claim 29 wherein the compound is sodium-9(N-formyl-N-methylaminomethylthio)-9-deoxyclavulanate.

54. A composition according to claim 29 wherein the compound is sodium 9-(N-formyl-N-methylaminomethylsulphonyl)-9-deoxyclavulanate.

55. A composition according to claim 29 in oral administration form.

56. A composition according to claim 29 in parentral administration form.

57. A composition according to claim 29 in topical application form.

58. A method according to claim 38 wherein the compound is p-nitrobenzyl-9-(acetamidomethylthio)-9-deoxyclavulanate.

59. A method according to claim 38 wherein the formula (II), (III), (V), (VI), (VII), or (IX):

$$\text{(II)}\quad CH_2-X-CHR_1-NH-CO-R_3$$

$$\text{(III)}\quad CH_2-X-CH_2-NH-CO-R_6$$

$$\text{(V)}\quad CH_2-X-CHR_8-NH-CO-R_9$$

$$\text{(VI)}\quad CH_2-X-CHR_{10}-NH-CO-R_{11}$$

$$\text{(VII)}\quad CH_2-X-CH_2-NH-CO-R_{11}$$

$$\text{(IX)}\quad CH_2-X-CHR_{12}-N(R_{13})(CO.R_{14})$$

or a pharmaceutically acceptable salt thereof wherein:
(i) in relation to formula (II) $R_1$ is hydrogen and $R_3$ is hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy and X is S, SO or $SO_2$;

(ii) in relation to formula (III) $R_6$ is hydrogen, phenyl, thienyl, furyl, phenyl mono-substituted by fluoro, chloro, lower alkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carbocylic acid lower alkyl ester, a carboxylic acid lower alkyl mono-substituted by phenyl, thienyl, furyl, or phenyl which is itself mono-substituted by fluoro, chloro, lower alkyl or lower alkoxyester, amino or aryl, and X is S, SO, or $SO_2$;

(iii) in relation to formula (V) $R_8$ is lower alkyl, phenyl, thienyl, furyl, phenyl mono-substituted by fluoro, chloro lower alkyl or lower alkoxy or lower alkyl mono-substituted by phenyl, thienyl, furyl, or phenyl which is itself mono-substituted by fluoro, chloro, lower alkyl or lower alkoxy; $R_9$ is hydrogen phenyl, thienyl, furyl, phenyl mono-substituted by fluoro, chloro, loweralkyl or lower alkoxy, lower alkyl mono-substituted by phenyl, thienyl, furyl, or phenyl which is itself mono-substituted by fluoro, chloro, lower alkyl or lower alkoxy, lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower ester, a carboxylic acid lower alkyl mono-substituted by phenyl, thienyl, furyl, or phenyl which is itself mono-substituted by fluoro, chloro, lower alkyl or lower alkoxy ester, amino or phenyl, thienyl, furyl, phenyl mono-substituted by fluoro, chloro, lower alkyl or lower alkoxy and X is SO or $SO_2$;

(iv) in relation to formula (VI) $R_{10}$ is hydrogen or lower alkyl and $R_{11}$ is lower alkyl mono-substituted by amino or by amino and by phenyl, thienyl, furyl, phenyl mono-substituted by fluoro, chloro, lower alkyl or lower alkoxy (v) in relation to formula (VII) $R_{11}$ is alkyl of up to 4 carbon atoms mono-substituted by amino or is alkyl of up to 4 carbon atoms mono-substituted by amino and by phenyl, thienyl, furyl, phenyl mono-substituted by fluoro, chloro, lower alkyl or lower alkoxy and X is S, SO or $SO_2$; and (vi) in relation to formula (IX) $R_{12}$ is hydrogen, lower alkyl, phenyl, thienyl, furyl, phenyl mono-substituted by fluoro, chloro, lower alkyl or lower alkoxy or lower alkyl or lower alkyl mono-substituted by phenyl, thienyl, furyl, or phenyl which is itself mono-substituted by fluoro, chloro, lower alkyl or lower alkoxy lower alkyl or lower alkyl mono-substituted by lower alkoxy, phenoxy, thienyloxy, furyloxy, phenoxy mono-substituted by fluoro, chloro, lower alkyl or lower alkoxy, carboxylic acid, a pharmaceutically acceptable carboxyl salt, a carboxylic acid lower alkyl ester, a carboxylic acid lower alkyl mono-substituted by phenyl, thienyl, furyl, or phenyl which is itself mono-substituted by fluor, chloro, lower alkyl or lower alkoxy ester, amino or phenyl, thienyl, furyl, phenyl mono-substituted by fluoro, chloro, lower alkyl or lower alkoxy, and $R_{14}$ is lower alkyl and X is S, SO or $SO_2$.

60. A composition according to claim 31 wherein the compound is in the form of a pharmaceutically acceptable salt selected from the group consisting of a sodium, potassium, calcium and magnesium salt.

61. A method according to claim 38 wherein the compound is p-nitrobenzyl 9-(acetamidomethylsulphinyl)-9-deoxyclavulanate.

62. A method according to claim 38 wherein the compound is of the formula (XIa):

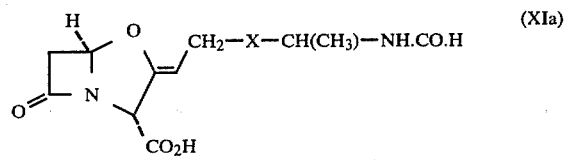

or a pharmaceutically acceptable salt thereof wherein X is S, SO or $SO_2$.

63. A method according to claim 38 wherein the compound is of the formula (XIb):

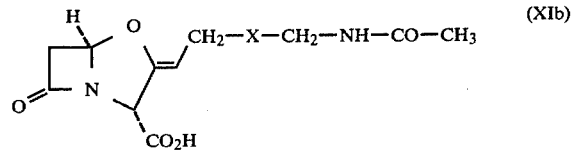

or a pharmaceutically acceptable salt thereof wherein X is S, SO or $SO_2$.

64. A method according to claim 38 wherein the compound is of the formula (XIV):

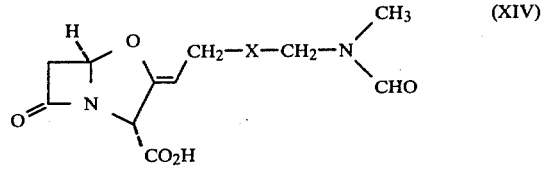

or a pharmaceutically acceptable salt thereof wherein X is S, SO or $SO_2$.

65. A method according to claim 38 wherein the compound is in the form of a pharmaceutically acceptable salt.

66. A method according to claim 65 wherein the salt is a sodium, potassium, calcium or magnesium salt.

67. A method according to claim 59 wherein the compound is in the form of a pharmaceutically acceptable salt selected from the group consisting of a sodium, potassium, calcium and magnesium salt.

68. A method according to claim 63 wherein the compound is in the form of a pharmaceutically acceptable salt selected from the group consisting of a sodium, potassium, calcium and magnesium salt.

69. A method according to claim 64 wherein the compound is in the form of a pharmaceutically acceptable salt selected from the group consisting of a sodium, potassium, calcium and magnesium salt.

70. A method according to claim 38 wherein the compound is p-nitrobenzyl 9-deoxy-9-thio[3'(R)-phenoxyacetamido-2-oxoazetidin-4(R)-yl]clavulanate.

71. A method according to claim 38 wherein the compound is sodium 9-deoxy-9-thio-[3'-(R)phenoxyacetamido-2-oxoazetidin-4(R)-yl]clavulanate.

72. A method according to claim 38 wherein the compound is p-nitrobenzyl 9-deoxy-9-thio(N-benzoylaminomethyl)clavulanate.

73. A method according to claim 62 wherein the compound is in the form of a pharmaceutically acceptable salt selected from the group consisting of a sodium, potassium, calcium and magnesium salt.

74. A method according to claim 38 wherein the compound is sodium 9-deoxy-9-thio(N-benzoylaminomethyl)clavulanate.

75. A method according to claim 38 wherein the compound is p-nitrobenzyl 9-(1-formamidoethylthio)-9-deoxyclavulanate.

76. A method according to claim 38 wherein the compound is p-nitrobenzyl 9-(1-formamidoethylsulphonyl)-9-deoxyclavulanate.

77. A method according to claim 38 wherein the compound is sodium 9-(1-formamidoethylthio)-9-deoxyclavulanate.

78. A method according to claim 38 wherein the compound is sodium 9-(1-formamidoethylsulphonyl)-9-deoxyclavulanate.

79. A method according to claim 38 wherein the compound is p-nitrobenzyl 9-(acetamidomethylsulphonyl)-9-deoxyclavulanate.

80. A method according to claim 38 wherein the compound is sodium 9-(acetamidomethylthio)-9-deoxyclavulanate.

81. A method according to claim 38 wherein the compound is sodium 9-(acetamidomethylsulphinyl)-9-deoxyclavulanate.

82. A method according to claim 38 wherein the compound is sodium 9-(acetamidomethylsulphonyl)-9-deoxyclavulanate.

83. A method according to claim 38 wherein the compound is p-nitrobenzyl 9-(N-formyl-N-methylaminomethylthio)-9-deoxyclavulanate.

84. A method according to claim 38 wherein the compound is p-nitrobenzyl-9-(N-formyl-N-methylaminomethylsulphonyl)-9-deoxyclavulanate.

85. A method according to claim 38 wherein the compound is sodium-9(N-formyl-N-methylaminomethylthio)-9-deoxyclavulanate.

86. A method according to claim 38 wherein the compound is sodium 9-(N-formyl-N-methylaminomethylsulphonyl)-9-deoxyclavulanate.

87. A method according to claim 38 wherein the administration is oral.

88. A method according to claim 38 wherein the administration is parentral.

89. A method according to claim 38 wherein the administration is by topical application.

* * * * *